US012245536B2

(12) United States Patent
Taylor et al.

(10) Patent No.: US 12,245,536 B2
(45) Date of Patent: Mar. 11, 2025

(54) SYSTEMS, METHODS, AND APPARATUSES FOR IMPLEMENTING AUTOMATED DATA MODELING AND SCALING OF A SOIL HEALTH DATA FABRIC

(71) Applicant: Arizona Board of Regents on behalf of Arizona State University, Scottsdale, AZ (US)

(72) Inventors: Todd Taylor, Mesa, AZ (US); Matthew Ikle, Alamosa, CO (US); William Brandt, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 555 days.

(21) Appl. No.: 17/511,288

(22) Filed: Oct. 26, 2021

(65) Prior Publication Data

US 2022/0124963 A1   Apr. 28, 2022

Related U.S. Application Data

(60) Provisional application No. 63/105,740, filed on Oct. 26, 2020.

(51) Int. Cl.
*A01B 79/00* (2006.01)
*G06F 18/214* (2023.01)
(Continued)

(52) U.S. Cl.
CPC ........ *A01B 79/005* (2013.01); *G06F 18/2148* (2023.01); *G06V 20/188* (2022.01); *H04L 9/3236* (2013.01); *H04L 9/50* (2022.05)

(58) Field of Classification Search
CPC .... A01B 79/005; A01B 79/02; G06V 20/188; G06V 20/13; G06V 20/17; G06V 20/194;
(Continued)

(56) References Cited

U.S. PATENT DOCUMENTS

2020/0019864 A1* 1/2020 Gu ...................... G05B 19/4183
2020/0359550 A1* 11/2020 Tran ........................ G06V 10/82

FOREIGN PATENT DOCUMENTS

AU    2008338805 A1 *  7/2010 ........... G01S 13/765
CN    110163233 A   *  8/2019
(Continued)

*Primary Examiner* — Jeffrey P Aiello
(74) *Attorney, Agent, or Firm* — Shumaker & Sieffert, P.A.

(57) ABSTRACT

An example system may implement automated data modeling and scaling of a soil health data fabric. For example, the example system may be configured to compile data measurements from disparate soil health data sources and integrate the data measurements with baseline soil samples, satellite imagery, or both. According to such an example, the system may train a machine learning algorithm using the integrated data measurements to determine most accurate local soil quality estimates and execute the machine learning algorithm to output soil quality estimate data models based on the data measurements. The example system may also train and refine local soil quality estimate data models to generate a regional soil quality estimate data model. In such an example, the system may scale the local and regional soil quality estimate data models and output soil quality estimates for a target region based on extended satellite imagery.

20 Claims, 12 Drawing Sheets

(51) Int. Cl.
  *G06V 20/10* (2022.01)
  *H04L 9/32* (2006.01)
  *H04L 9/00* (2022.01)

(58) Field of Classification Search
  CPC .. G06V 10/82; G06V 10/7784; G06V 10/764;
   H04L 2209/805; H04L 63/12; H04L
   9/3236; H04L 9/50; H04L 1/0057; G01N
   33/24; G01N 30/72; G01N 2033/245;
   G01N 22/04; G01N 27/223; G06F
   18/2148; G06F 18/2178; G06F 2218/00;
   G06F 30/27; G06Q 10/06395; G06Q
   10/067; G06Q 2220/00; G06Q 50/02;
   G06N 20/00; G06N 3/126; G06N 3/045;
   G06N 3/088; G06N 3/02; G06N 3/08;
   Y02P 90/80; H04W 4/38
  USPC ...... 700/108, 15, 275, 283; 702/2, 3, 22, 19,
   702/188, 5, 189, 190; 703/11, 6;
   707/999.102, 776
  See application file for complete search history.

(56) References Cited

FOREIGN PATENT DOCUMENTS

CN  107704493 B * 2/2021 ......... G06F 16/2255
FR  3019408 A1 * 10/2015 ............. G01W 1/10

\* cited by examiner

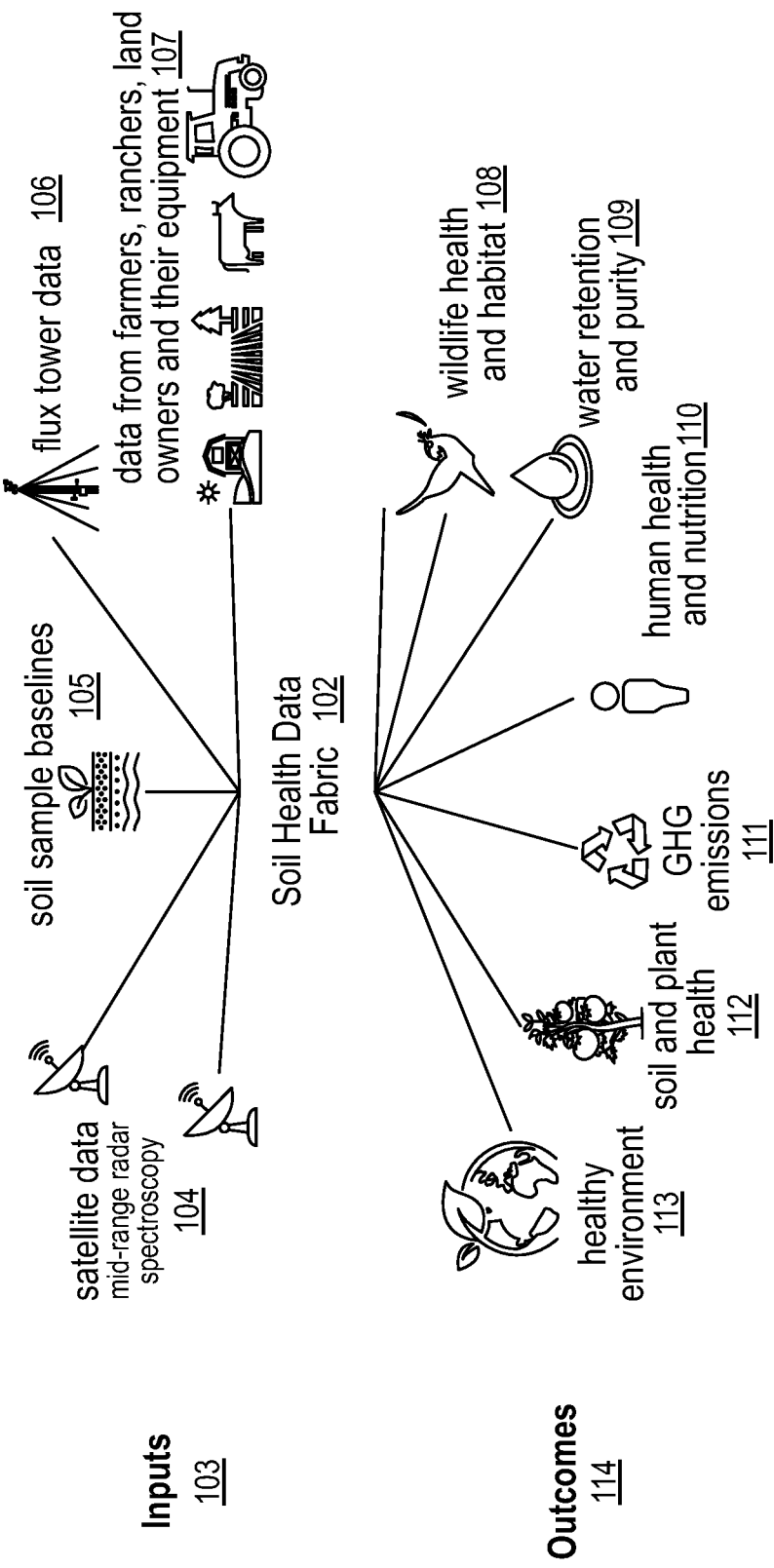

FIG. 4

400 – Table 1 

| Soil Health Quality Indicator 401 | Data Outputs 402 | Calculations of Soil Quality 403 |
|---|---|---|
| Soil organic carbon 404 | Soil organic carbon 404 | Biomass, flux tower data, AI methods, soil and genomic data inputs to ecosystem engine 405 |
| Soil structural stability: water-stable aggregates 406 | Aggregate analysis 407 | Ecosystem engine, indirect data inputs to DNNs and ANFIS, fractal geometry 408 |
| General microbial activity 409 | STCM, assays 410 | AI methods (decomposition models), ecosystem engine, flux tower data 411 |
| Carbon food source 412 | Active carbon measurements 413 | Soil organic matter fractions and soil climatic condition inputs to models, AI, and ecosystem engine 414 |
| Bioavailable nitrogen 415 | Soil organic matter protein 416 | Nitrogen transport and transformation process inputs to models, AI, and ecosystem engine 417 |
| Microbioal diversity: community structure 418 | Microbial biomass and community composition 419 | Fractal geometry and scalar inputs to models, AI, ecosystem engine, and multi-scale phenomena 420 |

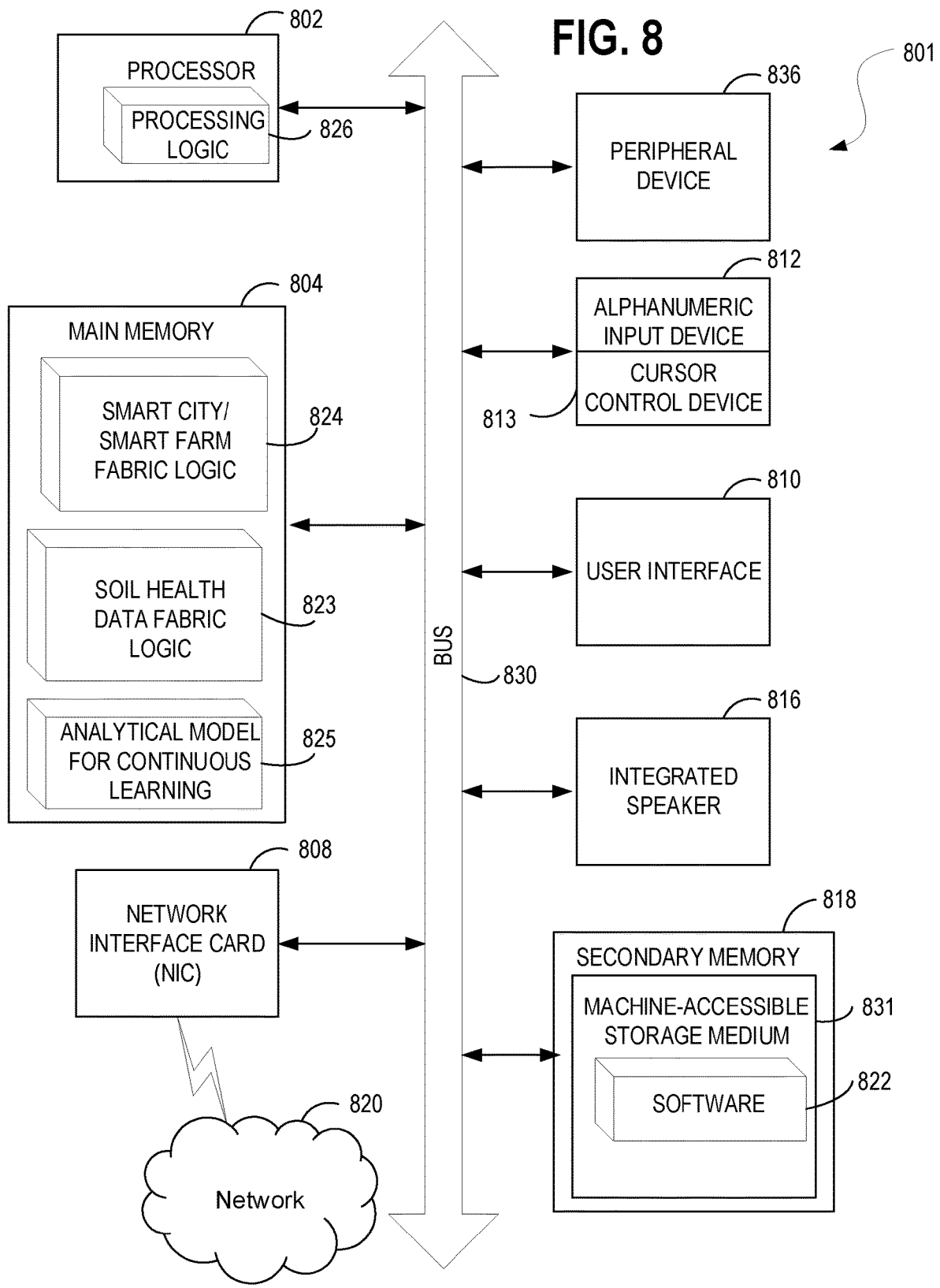

SYSTEMS, METHODS, AND APPARATUSES FOR IMPLEMENTING AUTOMATED DATA MODELING AND SCALING OF A SOIL HEALTH DATA FABRIC

CLAIM OF PRIORITY

This non-provisional U.S. Utility Patent Application is related to, and claims priority to the U.S. Provisional Patent Application No. 63/105,740, entitled "SYSTEMS, METHODS, AND APPARATUSES FOR IMPLEMENTING AUTOMATED DATA MODEL SHARING AND OPTIMIZATION OF A SMART FABRIC VIA ITERATIVE LEARNING ALGORITHMS," filed Oct. 26, 2020, the entire contents of which is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to soil science and computing and networking architectures, and more particularly, to systems, methods, and apparatuses for implementing automated data modeling and scaling of a Soil Health Data Fabric.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Carbon credits are part of a range of eco services offered by farmers. These are also known as carbon offsets and are traded in voluntary carbon markets.

Carbon credits can benefit agricultural landowners and operators such as farmers. Farmers adopting best practices that reduce carbon and greenhouse gas emissions through, for example, carbon sequestration and improved soil quality, may generate and sell carbon credits to large companies desiring to offset their carbon emissions in compliance markets based on governmentally imposed limits on greenhouse gas emissions or in voluntary markets. Typically, these large companies purchase carbon credits from a third-party aggregator who has paid the farmer for their production practices. Environmentally beneficial production practices that qualify for carbon credits include practices such as the introduction of cover crops, reducing tillage, crop rotation, use buffer strips, and other related best practices which result in overall improved soil carbon sequestration and reduced greenhouse gas emissions.

Carbon credits are typically based on the amount of carbon sequestered, which may be based on land acreage or per ton of carbon sequestered. Certain buyers of carbon credits will also pay for previously adopted carbon-sequestering practices before a farmer registered with a carbon program, thus incentivizing early adopters of agricultural conservation practices. Similarly, there are opportunities to track, trace, and verify other eco services beside carbon that is sequestered in the soil.

Problematically, the determination of carbon credits relies on methodologies that prove inaccurate and impractical in measuring the amount of carbon and other greenhouse gases that an area such as a plot of farmland or a whole geographic region can sequester. Such methodologies treat disparate agricultural areas equally regarding their ecological characteristics, specifically soil health and quality, that largely determine an area's carbon sequestration and greenhouse gas emissions. This leads to errors in the amounts of carbon credits that may be awarded to farmers and may result in underpayment of carbon credits to farmers by determining a lower amount of carbon sequestration than a parcel of land or a farm is actually sequestering. This error may translate into buyers paying more for carbon credits. A key factor driving the determination of carbon sequestration and microbiome in the soil is overall improved soil health and quality.

What is needed is a way to model soil health and quality across disparate regions for scaling of soil quality indicators and determining of carbon sequestration across areas of interest, and specifically, systems, methods, and apparatuses for implementing automated data modeling and scaling of a Soil Health Data Fabric.

BRIEF DESCRIPTION OF THE DRAWINGS

Embodiments are illustrated by way of example, and not by way of limitation, and can be more fully understood with reference to the following detailed description when considered in connection with the figures in which:

FIG. 1A depicts an exemplary Soil Health Data Fabric implementation having data integration across various inputs, in accordance with described embodiments;

FIG. 4 depicts exemplary Table 1 categorizing each of the six exemplary Natural Resource Conservation Service (NRCS) soil quality indicators including data outputs and calculation methods;

FIG. 8 illustrates a diagrammatic representation of a machine in the exemplary form of a computer system, in accordance with one embodiment.

DETAILED DESCRIPTION

Figure 1B:
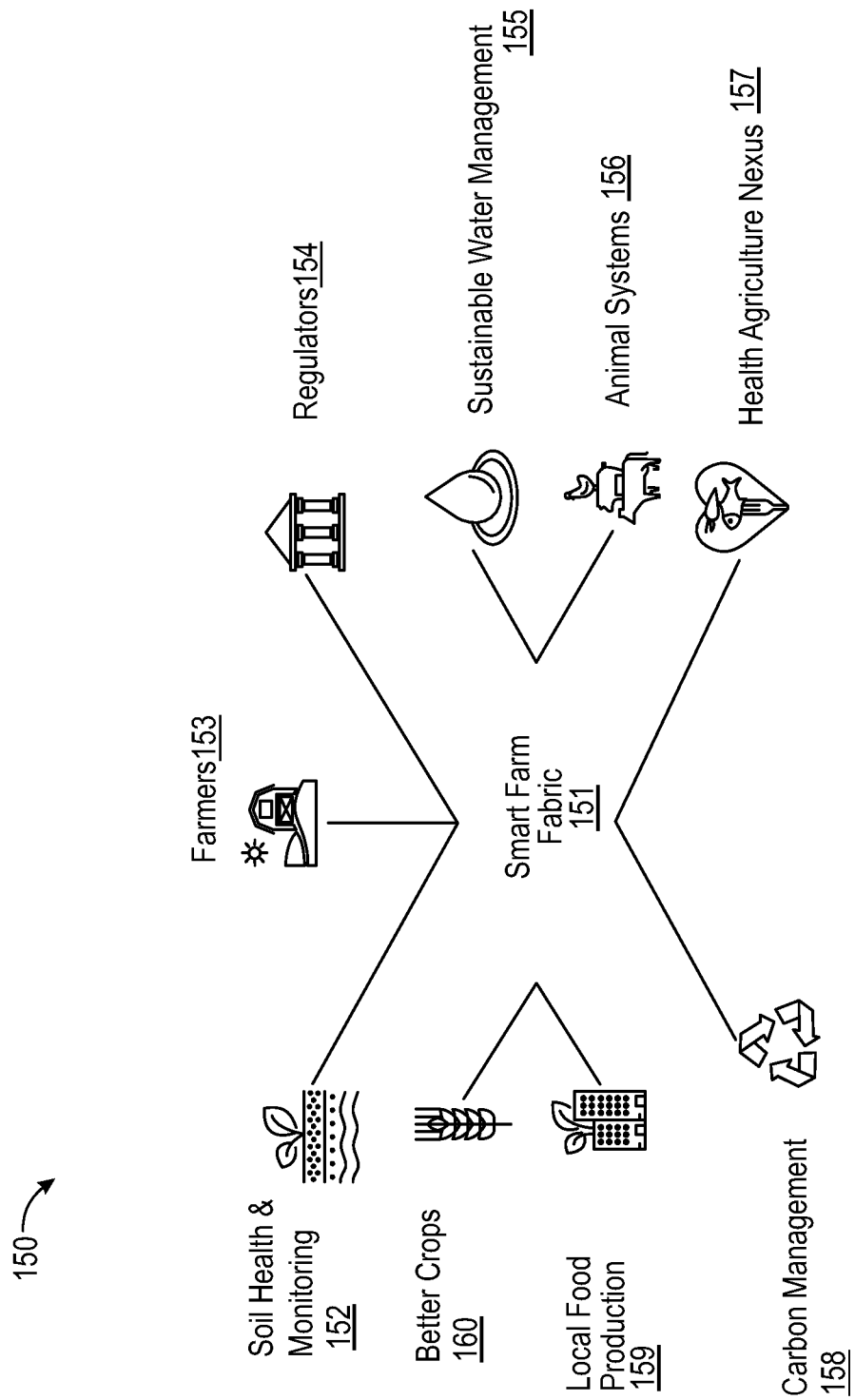
FIG. 1B depicts an exemplary Smart Farm Fabric implementation having data integration which provides for improvements to Nutritious Food, Thriving and Agile Farms, and eco-credit quantification and transactions.

Described herein are systems, methods, and apparatuses for implementing automated data modeling and scaling of a Soil Health Data Fabric.

For example, there is disclosed in accordance with a particular embodiment, a specially configured system having: a memory to store instructions; a processor to execute instructions stored in the memory; and stored logic within the memory that, when executed by the processor, causes the processor to perform operations including: compiling data measurements from disparate soil health data sources at a plurality of training data sites into a blockchain repository; integrating the data measurements with one or more of: (i) a plurality of baseline soil samples, and (ii) satellite imagery related to the plurality of training data sites to correlate soil health; training an AI algorithm using the integrated data measurements to determine most accurate local soil quality estimates; executing the AI algorithm to output a plurality of soil quality estimate data models based on the data measurements, in which the plurality of local soil quality estimate data models are based on pre-determined soil quality indicators; training the local soil quality estimate data models by comparing the local soil quality estimate data models to the plurality of soil samples; refining the local soil quality estimate data models via feedback processing to generate a regional soil quality estimate data model, in which the feedback processing applies transfer learning and feedback using additional data and comparison to the plurality of soil samples; scaling the local and regional soil quality estimate data models; and outputting soil quality estimates for a target region based on extended satellite imagery.

In the following description, numerous specific details are set forth such as examples of specific systems, languages, components, etc., in order to provide a thorough understanding of the various embodiments. It will be apparent, however, to one skilled in the art that these specific details need not be employed to practice the embodiments disclosed herein. In other instances, well-known materials or methods have not been described in detail in order to avoid unnecessarily obscuring the disclosed embodiments.

In addition to various hardware components depicted in the figures and described herein, embodiments further include various operations described below. The operations described in accordance with such embodiments may be performed by hardware components or may be embodied in machine-executable instructions, which may be used to cause a specialized or special-purpose processor programmed with the instructions to perform the operations. Alternatively, the operations may be performed by a combination of hardware and software.

Embodiments also relate to an apparatus for performing the operations disclosed herein. This apparatus may be specially constructed for the required purposes, or it may be a specially configured computer selectively activated or reconfigured by a computer program stored in the computer. Such a computer program may be stored in a computer-readable storage medium, such as, but not limited to, any type of disk including optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various specially configured computing systems may be used with programs in accordance with the teachings herein, or it may prove convenient to construct more specialized apparatus to perform the required method steps. The required structure for a variety of these systems will appear as set forth in the description below. In addition, embodiments are not described with reference to any particular programming language. It will be appreciated that a variety of programming languages may be used to implement the teachings of the embodiments as described herein.

Embodiments may be provided as a computer program product, or software, that may include a machine-readable medium having stored thereon instructions, which may be used to program a computer system (or other electronic devices) to perform a process according to the disclosed embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read-only memory ("ROM"), random access memory ("RAM"), magnetic disk storage media, optical storage media, flash memory devices, etc.), a machine (e.g., computer) readable transmission medium (electrical, optical, acoustical), etc.

Any of the disclosed embodiments may be used alone or together with one another in combination. Although various embodiments may have been partially motivated by deficiencies with conventional techniques and approaches, some of which are described or alluded to within the specification, the embodiments need not necessarily address or solve any of these deficiencies, but rather, may address only some of the deficiencies, address none of the deficiencies, or be directed toward different deficiencies and problems which are not directly discussed.

FIG. 1A depicts an exemplary Soil Health Data Fabric implementation 101 having data integration across various inputs, in accordance with described embodiments.

For accurate soil quality assessment, soil health indicators need to be measured to reach the goals of improving soil health and provide accurate determinations of carbon sequestration and greenhouse gas emissions for generating carbon credits for farmers.

Soil Health Data Fabric 102 involves the creation of a public, decentralized, and distributed data fabric allowing for users to measure, monitor, manage, quantify and begin to improve soil health. Using a collection of blockchain technologies coupled with advanced artificial intelligence (AI) and ecosystem modeling algorithms, this measurement capability may be implemented and importantly, done at scale using existing data sources.

Soil Health Data Fabric 102 is an integrated platform for quantifying soil health across large geographical areas that enables measurement of sequestered carbon and greenhouse gas emissions, as well as analysis of links between, for example, soil health and food nutrition, and water flow and retention. This information could eventually be exposed to end-user consumers of products from those farms. The tool could also be used by farmers to assess different agricultural methods across different parts of their farms to find the best mix of practices to maximize growing and financial potential.

Sequestered carbon and greenhouse gas emissions can vary widely based on the properties of agricultural lands and their soil. For example, a cornfield may sequester less carbon, and conversely emit more carbon and greenhouse gases, as a result of pesticide usage and harvesting activity that is commonplace in cornfields. On the other hand, some farmlands do not make significant use of pesticides, use fertilizer from livestock, and contain an ecosystem having sufficient foliage and an abundant supply of microorganisms that consume carbon and greenhouse gases as part of their biological processes. Such farmlands will have greater amounts of carbon sequestration and emit fewer greenhouse gases.

Soil Health Data Fabric 102 develops learning tools necessary to measure NRCS Soil Health Indicators at scale in commercial agriculture. Artificial intelligence and machine learning platforms may be involved in data aggregation and processing. Expertise in scalable AI models and blockchain integration is also needed. According to yet other embodiments, partnerships may implement the creation and application of blockchain technologies to improve data gathering, integration, accuracy, and transparency.

According to yet other embodiments, Soil Health Data Fabric 102 is implemented via a full-stack AI marketplace solution powered by a decentralized protocol via decentralized platform allowing AIs to cooperate and coordinate at scale. For example, AI solutions for implementation of the Soil Health Data Fabric 102 may be created using an advanced palette of technologies including deep neural net architectures, probabilistic logic, evolutionary program learning, and an artificial general intelligence engine which represents the forefront of hybrid neuro-symbolic AI. Using decentralized frameworks that emphasize an inter-AI collaboration framework, the Soil Health Data Fabric 102 may be implemented using state-of-the-art AI solutions to answer complex questions regarding the state and effects of soil health and quality. Outcomes 114 may include assessments of healthy environment 113, soil and plant health 112, GHG emissions 111, human health and nutrition 110, water retention and purity 109 (e.g., based on factors such as nitrogen and phosphorous), and wildlife health and habitat 108.

According to certain embodiments, the Soil Health Data Fabric 102 may be implemented in partnership with an agriculture technology company that assists farmers, suppliers, and manufacturers to augment their ability to make the best decisions for their land and maximize the value between environmental stewardship and economic profit. Using machine learning and artificial intelligence, the Soil Health Data Fabric 102 may leverage field data to improve yield, lower cost, reduce risk, and achieve sustainability goals for farmers.

According to certain embodiments, Soil Health Data Fabric 102 may utilize an AI-enabled software platform to analyze and manage complex farm datasets. Leveraging remote sensing, soil chemistry, and biogeochemical data in actionable agronomics, machine learning can extract important non-additive features from a fitted Random Forest, allowing the creation of a generalized additive model of yield. A machine learning engine provides farmers, crop consultants, and agricultural service partners cutting-edge scientific analysis that identifies the key field attributes driving crop yield.

The further integration of complex datasets creates an opportunity to understand agricultural soil functioning from local to regional scales, and to assess sustainable practices and their environmental impact.

Rationale and Significance.

The best way to measure soil health today is through soil samples such as soil sample baselines 105. However, it is cost and time prohibitive to pull soil samples every few feet across the nation/world. Soil health data fabric 102 creates a deep learning capability from random baseline soil samples 105 married to existing data sources, including satellite 104, sensor, flux tower 106, and farmer-supplied data 107.

According to certain embodiments, soil samples baselines 105 may be provided by mid-range radar, NASA GEDI ("Global Ecosystem Dynamics Investigation"), world view data applications, or flux tower 106 data repositories. According to yet other embodiments, soil samples baselines 105 may be physically collected and inspected, for instance, utilizing near infrared soil samplers and infrared spectroscopy for soil analysis.

According to certain embodiments, farmer-supplied data 107 may include direct data from farmers, ranchers, landowners, and their equipment. According to certain embodiments, sensors on farm equipment can upload farmer supplied data 107 as part of flux tower data 106.

As farmer-supplied data 107 may be provided largely voluntarily, it may be difficult to receive such data from farmers, ranchers, and landowners who are not compliant or interested in providing farmer-supplied data 107. Thus, procurement of farmer-supplied data 107 may be incentivized by offering carbon credits to farmers, ranchers, landowners, and farm operators (e.g., such as operators that farm rented land).

According to yet other embodiments, farmer-supplied data 107 may be provisioned onto a blockchain 701 to contribute payload data via a producer app. The producer app may serve as an interface for multiple inputs into a single asset on the blockchain 701. The producer app is a lightweight interface that allows farmers, ranchers, landowners to contribute information 107 directly to the smart farm fabric. According to other embodiments, a piece of farm equipment, using APIs, can contribute information 107 to the fabric directly. Similarly, a flux tower or other local imaging device can contribute information directly 106 to the platform on behalf of the farmer or landowner 107.

By building an extended learning model using advanced AI and soil ecosystem models (e.g., such as physics based models, agent based models and other methodologies of projecting or modeling soil), the Soil Health Data Fabric 102 will measure soil health on an ongoing basis without the need for constant soil sampling. These capabilities will enable us to track correlations between farming methods, inherent soil characteristics, and soil health, and thus form the basis for soil health improvement.

Approach.

Soil Health Data Fabric 102 creates an easy-to-use, real-time, ubiquitous measurement capability for soil health across each of the six NRCS soil health indicators 401. Soil Health Data Fabric 102 assesses soil health and quality across a target area through the completion of four objectives.

Objective 1: Gather together disparate data sources in a secure, immutable, decentralized, and distributed repository.

Objective 2: Used advanced analytics to create constantly maintained data models.

Objective 3: Align to each of the six NRCS soil quality indicators 401.

Objective 4: Extend soil quality measurements across different soil types, climates, regions, and topographies.
Methods.

Soil Health Data Fabric 102 is an easy-to-use tool, based on reliable, accurate, trustworthy, and resilient artificial intelligence systems, to provide ongoing estimates for the six NRCS soil health indicators 401. Soil Health Data Fabric 102 receives inputs including localized inherent soil and climate data such as soil sample baselines 105, and farmer-produced data 107. According to certain embodiments, this data is collected and aggregated by an artificial intelligence or machine learning platform. The tool will then output estimated values for each soil health indicator 401.

To lower uncertainty and increase accuracy, Soil Health Data Fabric 102 relies on multiple types of inputs, various AI technologies, including the latest hybrid neuro-symbolic methods, and ecosystem models. Redundant systems will help provide the necessary feedback to alleviate over-fitting and system sensitivity. Sub-symbolic AI models like deep neural networks (DNNs), for example, are extremely sensitive to input data and typically rely on large datasets of uniformly similar data making them difficult to use alone. Supplementing such systems with ensemble methods, ecosystem modeling, and neuro-symbolic AI tools will provide system feedback, enhancing trust, accuracy, and resilience, while reducing uncertainty.

Data Inputs.

Data Inputs for all soil quality indicators 401 include data measurements from disparate soil health data sources such as:

Flux Tower Emissions 106
Satellite Data 104 (myriad of wavelengths/types, LIDAR)
Climate
Soil composition
  Soil pH
  Soil texture including multi-scale fractal features
  Soil bulk density
  Soil organic matter
  Particulate organic matter
  Soil genomics
  Soil metagenomics
Geophysical
  Boundary/Geolocation
  Hydrology
  Chemical
  Biological
  Genomic
Aggregated Data
  Yield
  Soil Sample
  Metagenomic Samples
  EC/EM/Soil Texture
  Planting
  Application
    Fertilizer
    Chemical
    Field Boundary
    Topography FIG. 1B depicts an exemplary Smart Farm Fabric implementation 150 having data integration which provides for improvements to Nutritious Food, Thriving and Agile Farms, and eco-credit quantification and transactions.

So-called "Smart Cities" are often characterized by small and isolated projects with siloed data separated from business processes and applications. That is to say, these various small and isolated projects have no means by which to intercommunicate with one another, much less collaborate for their collective benefit.

The technological aspects of smart cities are layered and complex, and often face competing priorities such as balancing cost with implementing viable solutions within a reasonable period of time and the issue of a fragmented landscape of devices, networks, security models, and end-to-end applications, all of which seek to deliver competing features and benefits for different stakeholders.

A smart fabric aims to reduce complexity, increase interoperability, and facilitate the delivery of proposed solutions on time and on budget while enabling the interoperability missing from current smart city technology frameworks. Such interoperability includes the integration and collaboration of Internet of Things (IoT) data streams with features and functionality that may consume such IoT data downstream.

Unfortunately, delivering such capabilities up-front with conventional smart city technology platforms proves to be a daunting task due to the cost, complexity, and time required to realize such functionality. Without such functionality, smart cities lack the ability to benefit from the vast amounts of data that would be available if citywide IoT data stream intercommunication were provided.

Further still, even where intercommunication capabilities exist, there is no means presently available to the marketplace by which to implement continuous improvement based on the data available within a smart city's communication infrastructure.

Improved systems are needed which provide less complex communication means and facilitate continuous improvement.

As shown here, the Smart Farm Fabric implementation 150 provides data and communication interconnectivity between farmers 153 and a variety of other entities, including regulators 154, sustainable water management entities 155, animal systems 156, health agriculture nexus systems 157, carbon management platforms 158, local food production operators 159, better crop monitoring systems 160, and soil health and monitoring utilities 152. According to certain embodiments, soil health and monitoring 152 is implemented via soil health data fabric 102.

In such a way, the Smart Farm Fabric implementation 150 provides an integrated, trusted platform to quantify carbon emissions and sequestration, amongst other benefits.

According to certain embodiments, the platform correlates the data from all the farms, sensors, samples, and satellites providing information. Once such data is correlated in a distributed ledger (e.g., within a blockchain or other DLT based technology), "learning" algorithms iteratively process the data and operate to pinpoint automatically learned factors that are predicted to lead to optimal soil and crop production, water conservation, and proper quantification of carbon credits and debits.

Similar to the issues of data segregation discussed above in the context of the Smart City Fabric 500, prior known solutions in the farming and agriculture space similarly suffer from data segregation. Stated differently, the isolated efforts and data will not improve the current environmental situation which is leading to degenerating soil, worsening food nutrition, as well as wasted and contaminated water.

Figure 2:
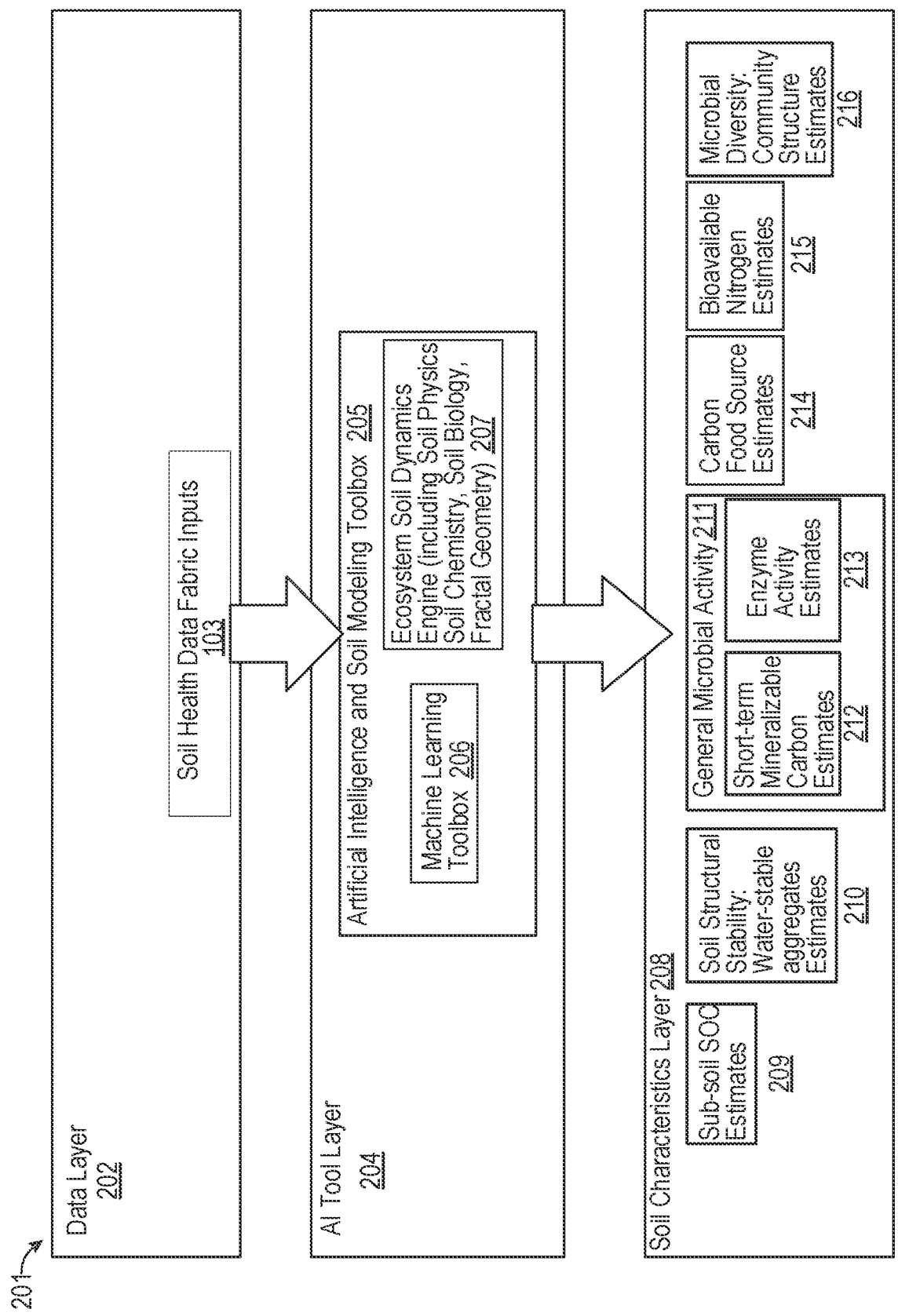
FIG. 2 depicts an exemplary flow of inputs to Natural Resource Conservation Service (NRCS) soil health indicators, in accordance with described embodiments.

FIG. 2 depicts the flow of inputs to Natural Resource Conservation Service (NRCS) soil health indicators 201, in accordance with described embodiments.

As previously discussed, different areas of land do not have equal properties when it comes to soil health, carbon sequestration, and greenhouse gas emissions. Likewise, it is often not practical to assess soil sample baselines 105 and soil health quality indicators directly across large areas of interest that may include challenging topography, climate conditions, and may require massive resources and time that surveyors or data collectors do not have.

Data from farmers, ranchers, landowners, and their equipment 107 which is transmitted as, for example, flux tower data 106 may be integrated spatially with satellite data 104 including satellite imagery providing detailed and granular views of a region of interest. Additional data, such as soil sample baselines 105 if available, may supplement this data. Such integration of soil health data fabric inputs 103 in data layer 202 allows for correlating soil health with macroscopic indicators such as foliage.

For example, according to a particular embodiment, accurately estimating the soil health and generating the soil health data fabric inputs (e.g., data inputs 103) is realized through the use and capture of remote sensing data. Remote sensing has been successfully applied to predict a variety of conditions, including, for example socioeconomic indicators. For instance, recent innovations have provided convenient and scalable methods for estimating various indices relying on nighttime lights, satellite imagery, and emerging machine learning models, whereas prior successful techniques tend to leverage the correlation between lit areas and GDP values, thus enabling the detection of detailed land appearances thought to be strongly correlated with socioeconomic statuses, such as buildings, cars, roads, and farmlands.

According to certain embodiments, data layer 202 may interface with AI tool layer 204. Artificial intelligence and soil modeling toolbox 205 may include a machine learning toolbox 206 and an ecosystem soil dynamics engine 207. Ecosystem soil dynamics engine 207 may include tools based on various scientific and mathematical disciplines such as soil physics, soil chemistry, soil biology, and fractal geometry.

According to certain embodiments, AI tool layer 204 may estimate local soil quality based on Soil Health Data Fabric inputs 103 from data layer 202 and may develop soil quality estimation models.

According to certain embodiments, AI tool layer 204 may configure artificial intelligence and soil modeling toolbox 205 to refine models and better assess soil health data fabric inputs 103 from data layer 202. According to certain embodiments, such configurations may be based on soil characteristics layer 208, which includes each of the six exemplary Natural Resources Conservation Service (NRCS) soil quality indicators 401 as will be further discussed in FIG. 4—Table 1. NRCS soil quality indicators 401 include sub-soil SOC estimates, soil structure stability: water-soluble aggregates estimates 210, general microbial activity 211 (which includes short-term mineralizable carbon estimates 212 and enzyme activity estimates 213), carbon food source estimates 214, bioavailable nitrogen estimates 215, and microbial diversity: community structure estimates 216.

Soil Health Data Fabric 102 provides real-time regional, and ultimately global, soil quality measurement estimates, leading to true scalability. According to certain embodiments, scalability may involve extending satellite imagery and soil health data across a target area.

Figure 3:
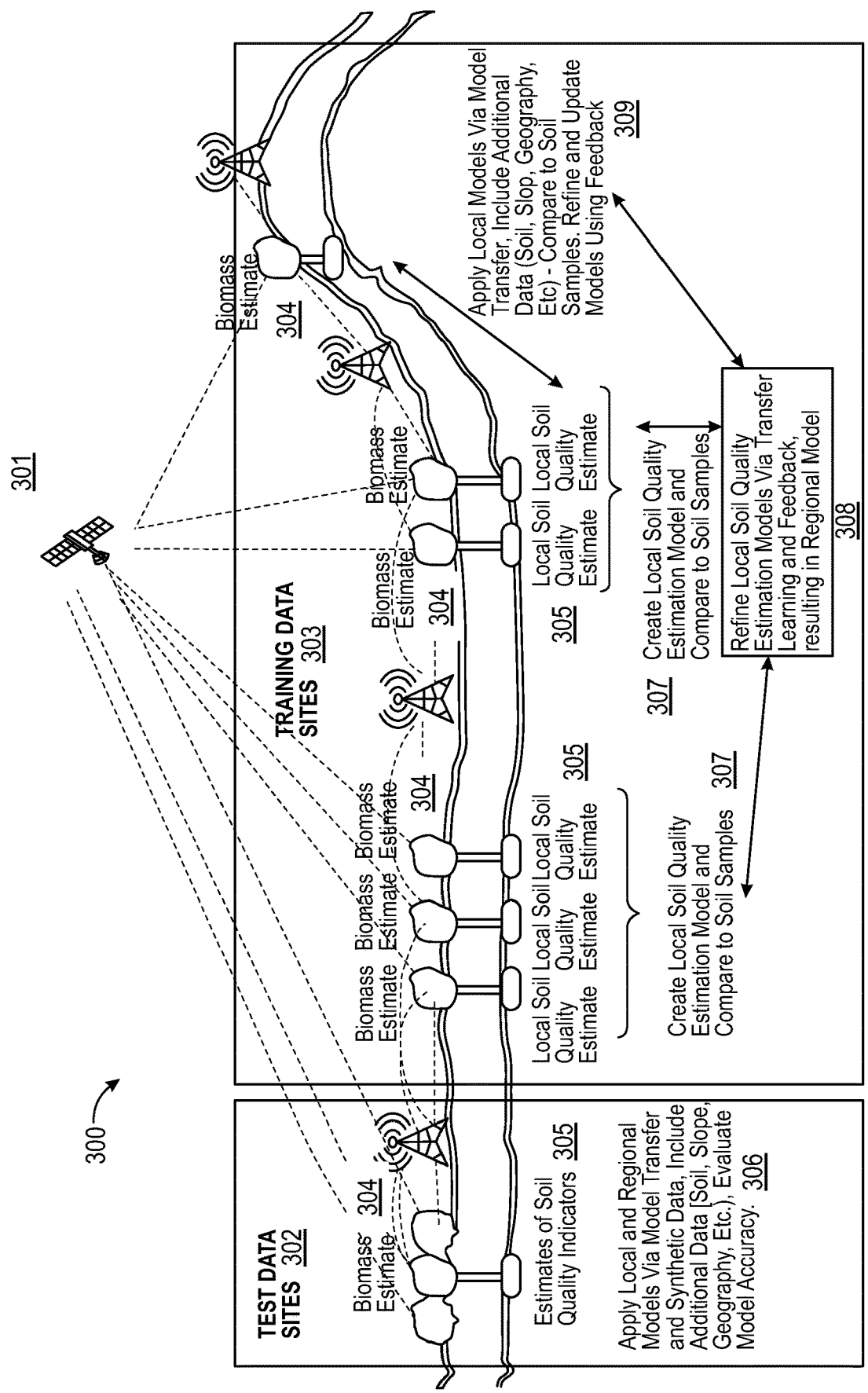
FIG. 3 depicts an exemplary mapping of test data and training data sites for soil quality estimation model generation and refinement, in accordance with described embodiments.

FIG. 3 depicts an exemplary mapping of test data and training data sites for soil quality estimation model generation and refinement 300, in accordance with described embodiments.

As depicted here, satellite imagery 301 and soil health data 304 may be extended across larger geographic areas, including various test data sites 302 and training data sites 303. Biomass estimates 304 are collected at these various sites and transmitted as satellite data 301. According to certain embodiments, satellite data 301 may include satellite imagery collected at various test data sites 302 and training data sites 303. At training sites 303, local soil quality estimates 305 are assessed to create local soil quality estimation models and compare to soil samples 307. Next, the local soil quality estimation models are refined via transfer learning and feedback, resulting in a regional model 308. Still further, the local models are applied via model transfer and may include additional data such as soil, slope, geography, and other data points. The local models are compared to soil samples and refined and updated using received feedback 309. A final step in the training and test process includes estimating soil quality indicators 305 at test data sites 302, followed by applying local and regional models via model transfer and synthetic data, including additional data such as soil, slope, geography, etc. in order to evaluate model accuracy 306.

According to certain embodiments, test sites 302 and/or training data sites 303 may include research farms or managed lands having dense data.

For example, according to the various embodiments, different machine learning and soil modeling methods may be applied depending upon which soil quality characteristic is being estimated or, stated differently, depending upon which particular soil quality characteristic is being optimized for by the target modeling methodology. This is because different soil quality indicators require different sensors and measurement tools as well as different processing methods to obtain such estimates.

For instance, according to a particular embodiment, available USDA's Natural Resources Conservation Service ("NRCS") soil indicators are selected to align with specific machine learning and modeling methods. For instance, according to such an embodiment, so as to estimate sub-soil sequestered carbon, satellite and other above-ground imagery is utilized in conjunction with Convolutional Neural Networks (CNNs) to obtain an estimate of above-ground biomass levels. To obtain local sub-soil carbon estimates one still needs to rely on ecosystem modeling based upon the estimated above-ground bio-mass. Consequently, this estimate may then later be combined with additional sensor data, such as gas emission flux tower data, soil genomics and meta-genomics, etc., to improve accuracy using, for example, a variety of AI ensemble methodologies including one or more of bagging, boosting, stacking, and so forth. Local estimates for the other soil quality estimates would require different sets of tools applied to different sets of inputs. Thus, according to certain embodiments, the implementation specifically incorporates sets of AI/ML tools.

Within the context of machine learning, a Convolutional Neural Network (CNN, or ConvNet) is a class of deep neural networks, which may be applied to analyzing various forms and sources of input data. Convolutional Neural Networks are regularized versions of multilayer perceptrons. Multilayer perceptrons are fully connected networks, such that each neuron in one layer is connected to all neurons in the next layer, a characteristic which can lead to a problem of overfitting of the data, and thus the need for model regularization. Convolutional Neural Networks thus seek to apply model regularization, but with a distinct approach. Specifically, CNNs take advantage of the hierarchical pattern(s) found within the input data to assemble more complex patterns using smaller and simpler patterns. Consequently, on the scale of connectedness and complexity, CNNs represent the lower extreme.

According to additional embodiments, non-invasive and highly scalable measurement operations are utilized. For instance, prior methodologies often required estimating sub-soil sequestered carbon through the use of costly and time-consuming laboratory analysis based on numerous physical soil samples obtained on regular schedules.

However, by utilizing non-invasive and automated sensors and measurement tools to provide proxy measurements, greater scalability may be attained. This is because more frequent analysis cycles are possible due to the automated and non-invasive nature of the data collection which thus provides for a more scalable, automated, and lower-cost solution than needing to rely on periodic hand-gathered physical samples.

Other benefits are also realized through the non-invasive and more frequent data collection scheme. Specifically, there is a problem with prior methodologies resulting from a lack of granularity. Specifically, sub-soil carbon levels can vary quite drastically over small distances due to hyper-local land characteristics, such as soil type, topography, geology, climate variations, etc. To overcome this variability and enable scaling of sub-soil carbon estimates across local regions, disclosed embodiments leverage not only the more frequent and non-invasive data collection, but further utilize the input data and ecosystem modeling to create synthetic data for use in, for example, transfer learning algorithms.

Within the context of AI and machine learning, transfer learning focuses on storing knowledge gained while solving one problem and applying that storage knowledge to a different yet related problem. In such a way, the trained machine learning models are enabled to re-use or "transfer" information and knowledge learned from previously learned tasks for the learning of new tasks which results in significantly improved efficiency for the reinforcement learning agent responsible for generating the trained AI model.

FIG. 4—Table 1 depicts each of the six exemplary Natural Resources Conservation Service (NRCS) soil quality indicators 401 including data outputs 402 and calculation methods 403.

1. Organic Matter Cycling and Carbon Sequestration: Soil Carbon (SOC).

The first NRCS soil quality indicator 401 is soil organic carbon 404 which may be outputted 404 using standard operating procedure. Calculation methods 405 include Deep Neural Networks (DNNs) which have been shown to provide good estimates of above-ground biomass. Soil modeling uses biomass estimates to obtain good localized estimates of sub-soil SOC. Flux tower emission measurements 106 provide supplemental estimates that will help reduce variability and uncertainty. The various inputs suggest that AI ensemble methods (bagging, boosting, stacking, etc.) and/or neuro-symbolic AI methods could further reduce variability and uncertainty. The ecosystem engine, supplied with additional soil and genomic/metagenomic data, will apply soil physics, chemistry, and biology modeling to estimate subsoil SOC.

2. Soil Structural Stability: Water-Stable Aggregates.

The second NRCS soil quality indicator 401 is soil structural stability: water-stable aggregates 406 which may include as output an aggregate analysis 407 to determine the size distribution of water-stable aggregates and the amount of aggregation. Calculation methods 408 include the ecosystem simulation engine estimating the complex physical, chemical, and biological processes involved in aggregates. DNNs and Adaptive Neuro-Fuzzy Inference Systems (ANFIS) provide reasonable estimates of soil aggregate stability (SAS) based upon indirect data including clay, organic matter, and pH. Fractal geometry has also been shown to be another property that could be used to estimate SAS.

3. General Microbial Activity.

The third NRCS soil quality indicator 401 is general microbial activity 409, which may include as output short-term carbon mineralization (STCM) and assays 410. Assays may include traditional, bench-scale assays for β-glucosidase, N-acetyl-β-D-glucosaminidase, phosphomonoesterases, and arylsulfatase using the US Department of Agriculture NRCS standard operating procedures. Calculation methods 411 may include AI ensemble methods (boosting, bagging, stacking) coupled with an ecosystem engine and neurosymbolic AI. According to certain embodiments, decomposition models may also be used as decomposition occupies a central position in global biogeochemical cycles and mathematical models play a central role in efforts to understand them and predict future changes. Decomposition models span a wide range of temporal, spatial, and hierarchical scales of resolution, from physiologically based simulations of microbial activity in laboratory cultures to empirical models that estimate gas flux dynamics over regional landscapes. As a result of this observation, flux tower measurements 106 are one source of inputs into a multi-scale "inverse-problem" model.

4. Carbon Food Source.

The fourth NRCS soil quality indicator 401 is carbon food source 412, which may include as output measurements of active carbon 413, also known as permanganate-oxidizable carbon (PDXC) or reactive carbon (RC). Calculation methods 414 may include AI soil organic matter (SOM) fractions from which reactive carbon originates. These fractions include fresh organic material, soil microbial biomass, particulate organic matter, and other easily metabolized organic compounds such as carbohydrates (sugars), and proteins (amino acids) as well as carbon loosely bound to soil minerals.

Moreover, soil climatic conditions are inherent factors influencing the mineralization rates of organic carbon and, concomitantly, the accumulation or decline of the quantity of reactive carbon in soil organic matter. Clay minerals can strongly bind soil organic matter and protect it along with the associated reactive carbon from rapid mineralization, whereas sand and silt are non-binding. Very poor drainage creates anaerobic conditions that favor the formation of methane ($CH_4$), inducing a systemic loss of carbon and a decline in total organic carbon (TOC) and reactive carbon contents. The combination of inherent soil climatic factors with dynamic factors, including microbial biomass levels and aggregate stability would benefit from calculations methods 414 that include the combination of ensemble methods, neuro-symbolic AI, and an ecosystem engine.

5. Bioavailable Nitrogen.

The fifth NRCS soil quality indicator 401 is bioavailable nitrogen 415, which may include as output soil organic matter protein 416 which measures bioavailable nitrogen by extracting protein from the organic matter in soil samples using an autoclaved citrate extractable (ACE) protein procedure. Calculation methods 417 take into consideration numerous inherent factors impacting nitrogen transport and transformation processes. Such inherent factors include soil drainage, soil texture, slope steepness, climate (rainfall and temperature), moisture, soil aeration, etc. The potential for leaching is dependent on soil texture (percentage of sand, silt, and clay), as well as soil water content. A combination of ensemble models, neuro-symbolic AI, and an ecosystem engine is well suited for implementing these calculation methods.

6. Microbial Diversity: Community Structure.

The sixth NRCS soil quality indicator 401 is microbial diversity: community structure 418, which may include as output microbial biomass and community composition 419 as measured through a high-throughput Neutral Lipid Fatty Acids (NLFA) and Phospholipid Fatty Acids (PLFA) analysis of soil using standard operating procedures. Calculation methods 420 take into consideration that microbial community diversity is extraordinarily complex, displaying self-similarity at multiple spatial scales, suggesting fractal geometric structures and asynchrony among microbial taxa whereby different soil fungi and bacteria promoted different ecosystem functions at different times. Again, the combination of ensemble models, neuro-symbolic AI, and an ecosystem engine is well suited for implementing these calculation methods.

Figure 5:
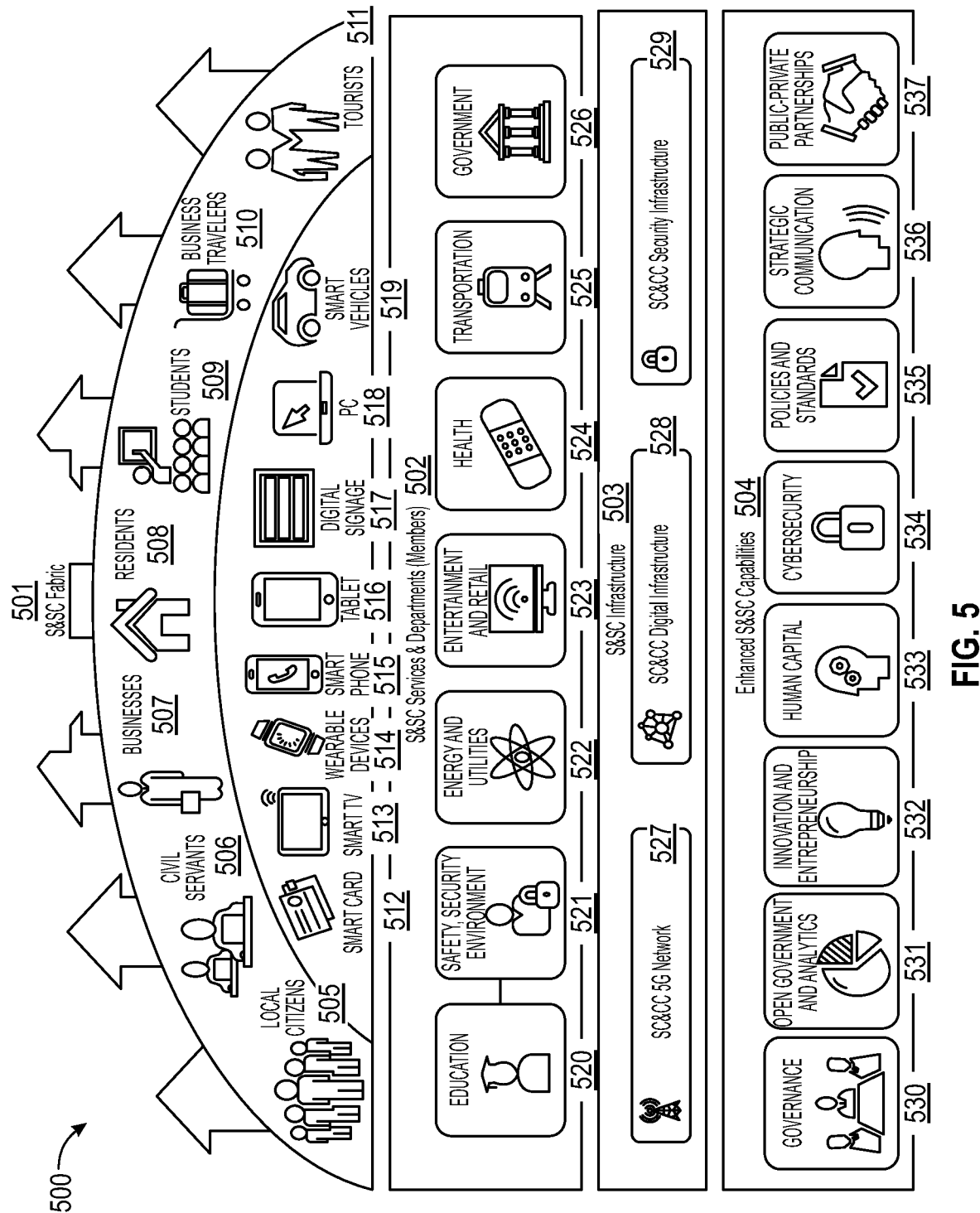
FIG. 5 depicts an exemplary Smart City Fabric implementation having data integration across services and departments, in accordance with described embodiments.

FIG. 5 depicts an exemplary Smart City Fabric implementation 500 having data integration across services and departments, in accordance with described embodiments.

For instance, disclosed in greater detail below is a Smart City Fabric which allows for quick and automated information sharing and data model maintenance. Such a platform allows for data models to be maintained and algorithms to run on an iterative basis, thus permitting the algorithms to become smarter over time. This addresses the problem that it is only possible to improve that which we can measure and monitor. Through the continuous monitoring of available data, such as IoT data streams available from a city's smart fabric, it is possible to incrementally improve and ultimately optimize the Smart City Fabric over time. Currently, cities are measuring and monitoring data only within their respective department silos, thus representing a significant lost opportunity for improvement due to the lack of visibility to data within other department silos or zones and due further to the lack of analysis of the available data present within a given Smart City, regardless of whether such data is presently accessible.

In related embodiments, there is further disclosed a Smart Farm Fabric 150 (see FIG. 1B), providing a platform by which to correlate data generated across multiple interconnected farms, including IoT data streams emanating from sensors, samples, and satellites providing information. Once such data is collected, aggregated, and/or correlated within a distributed computing system, "learning" algorithms iteratively analyzing the data will then learn to pinpoint the factors that lead to optimal soil and crop production, product genealogy, water conservation. Such analysis may thus be utilized, for example, in the proper quantification and allocation of carbon credits or debits.

The reality is that present-day isolated efforts which are limited due to the inherent nature of data silos simply cannot improve the confluence of current environmental, economic, and political conditions which are leading to degenerating soil, food nutrition, and wasted or contaminated water.

Improved systems are needed which provide less complex communication means and facilitate continuous improvement across varied data sources for the overall betterment of society and ultimately for the more effective use of resources, be they within a Smart City Fabric or a Smart Farm Fabric implementation.

As shown at the bottom layer of the Smart City fabric implementation 500, there is an enhanced S&SC capabilities layer 504, having therein each of various capabilities including (from left to right): governance 530, open government and analytics 531, innovation and entrepreneurship 532, human capital 533, cybersecurity 534, policies and standards 535, strategic communication 536, and public-private partnerships 537.

A second layer is further depicted providing the S&SC infrastructure layer 503, which includes SC&CC 5G network 527, SC&CC digital infrastructure 528, and SC&CC security infrastructure 529.

The third layer depicts the S&SC services and departments (e.g., Members) layer 502, which depicts various exemplary services and departments, including (from left to right): education 520, safety, security, and environment 521, energy and utilities 522, entertainment and retail 523, health 524, transportation 525, and government 526.

Each of the first, second, and third layers (504, 503, and 502 respectively) are communicably interconnected with and ultimately inform the S&SC fabric 501, providing data and analytics to the Smart City Fabric implementation 500 to various consumers and entities such as local citizens 505, civil servants 506, businesses 507, residents 508, students 509, business travelers 510, and tourists 511, with such data including information emanating from and being consumed by IoT devices and IoT streams such as: smart cards 512, smart TVs 513, wearable devices 514, smartphones 515, tablets 516, digital signage 517, PCs 518 and smart vehicles 519.

In such a way, the Smart City Fabric implementation 101 provides a platform that allows for the integration of necessary smart city assets, devices, sensors, departments and their corresponding systems, a smart city ledger, and reporting and analytics capabilities for all city constituents and services.

According to certain embodiments, an immutable record of transactions is utilized (e.g., such as a blockchain or other "DLT"/Distributed Ledger Technology) for storing the record of transactions as a city-wide ledger that automatically reconciles, distributes, and receives funds and provides visibility to departments and customers.

According to such embodiments, there is further provided a single, shared view of citizenry, assets, and business customers based on the underlying data stored within the city-wide ledger. For instance, with such information being provided on demand from a public blockchain.

Further provided are various automation, reporting, and analytics capabilities provided across functions, devices, sensors, and systems which further enhance the user experience as well as improve the data repository upon which the iterative analytics may operate to continuously learn, improve, and optimize the Smart City Fabric implementation 500.

The described embodiments provide for enhanced security due to the immutable ledger which, according to certain embodiments, further requires DLT and blockchain type safeguards, including by way of example, consensus requirements prior to acceptance of a transaction onto a primary chain, segregation of information, heightened use of encryption and digital keys, as well as digital identity.

Still further, improved security is provided for utility grids and other potentially vulnerable city systems which are often at greater risk of intrusion or other malfeasance when based on prior known systems and methods.

In such a way, the Smart City Fabric implementation 500 provides for cross-department analytics which are purposefully enabled by a holistic data model. Higher-level applications which are built atop the holistic data model then utilize Machine Learning (ML), Artificial Intelligence (AI), Robotic Process Automation (RPA), and scenario analysis capabilities to drive continuous improvement through constant iterative learning based on data and metrics made accessible via the Smart City Fabric implementation 500 shown here.

The Smart City Fabric thus allows for quick and automated information sharing and data model maintenance. Such a platform allows for data models to be maintained and algorithms to run and become smarter over time. It is only possible to improve that which is measured and monitored. Unfortunately, prior known systems, including the most advanced cities, are measuring and monitoring only within their respective department silos, thus rendering citywide interdepartmental learning and analytics wholly impossible.

Described embodiments, therefore, provide the opportunity or massive technological advancement for smart cities of all sizes, regardless of where such cities may be geographically located. This is because previously known technologies and software are built to service the need of single companies, single departments, or single entities. Through the use and practice of the Smart City Fabric implementation 500, as depicted here, there is provided the capabilities for a data, security, membership, and process framework for any ecosystem-level or city-wide application.

Figure 6:
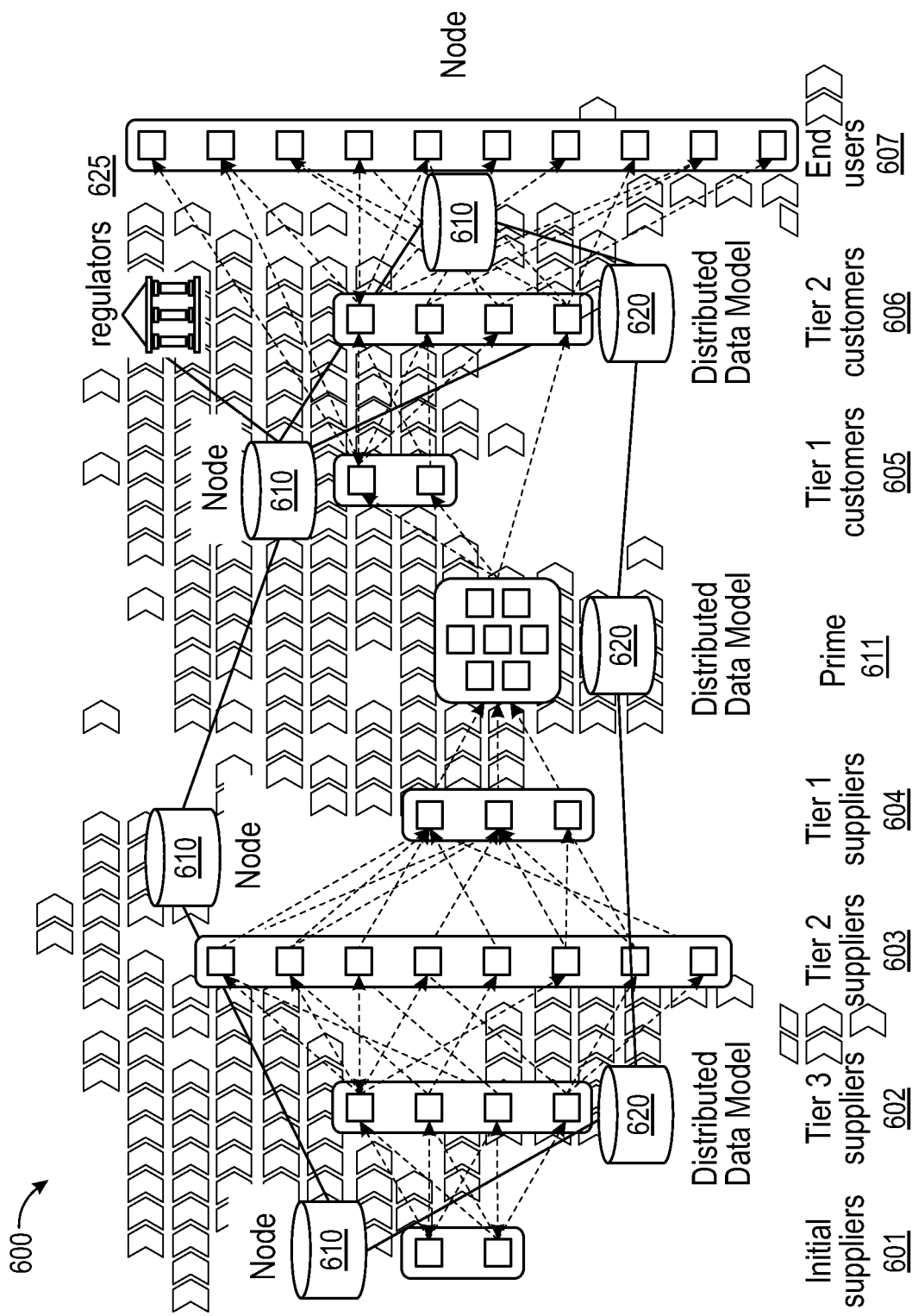
FIG. 6 depicts an exemplary network data model utilizing distributed data model structure, in accordance with described embodiments.

FIG. 6 depicts an exemplary network data model 600 utilizing distributed data model structure, in accordance with described embodiments.

As depicted here, there are multiple "nodes" 610 which are interconnected with the distributed data model 620. As shown here, there are multiple copies of the "ledger" which is stored and persisted by the distributed data model 620. Different entities may access the distributed data model 620, such as the initial suppliers 601, tier 3 suppliers 602, tier 2 suppliers 603, and tier 1 suppliers 604. Similarly, various downstream supply chain entities may also access the distributed data model 620, such as tier 1 customers 605, tier 2 customers 606, and ultimately, end users 607.

Using a collection of distributed compute and related technologies, a novel smart farm fabric implementation is thus provided which utilizes a specialized framework for network data model creation and continual maintenance.

Using enterprise-centric data models, optimization, and advanced analytics, the challenge of optimizing processes beyond the four walls of a given company has heretofore proven to be impossible because of access restrictions preventing any centralized analytical or machine learning engine access to such data or maintenance of the data needed that ultimately affords ongoing data model persistence and thus the opportunity for continuous and iterative learning.

However, by leveraging distributed computing models and technologies, such as DLT and blockchain technologies upon which data may be immutably stored in a secure and publicly accessible manner, the Smart Farm Fabric implementation 151 described herein utilizes specialized systems and platforms that span multiple companies and entities. These capabilities provide the Smart Farm Fabric implementation 151 with the ability to capture product, transaction, and process flow information across an entire value chain, ecosystem, or network, such as the Smart Farm Fabric 150 depicted at FIG. 1B or the Smart City Fabric 500 described at FIG. 5 above.

With such data having been captured and appropriately stored, it is thus possible for the Smart Farm Fabric implementation 151 to not only create and maintain network-wide data models, but also to apply analytics and algorithms against those data models in order to iteratively and continuously optimize and improve the interactions and efficiency of an entire network of companies and their related interactions. Thus, the Smart Farm Fabric implementation 151 provides benefits not just for single-tier networks but also across multiple tiers of a value chain.

Figure 7A:
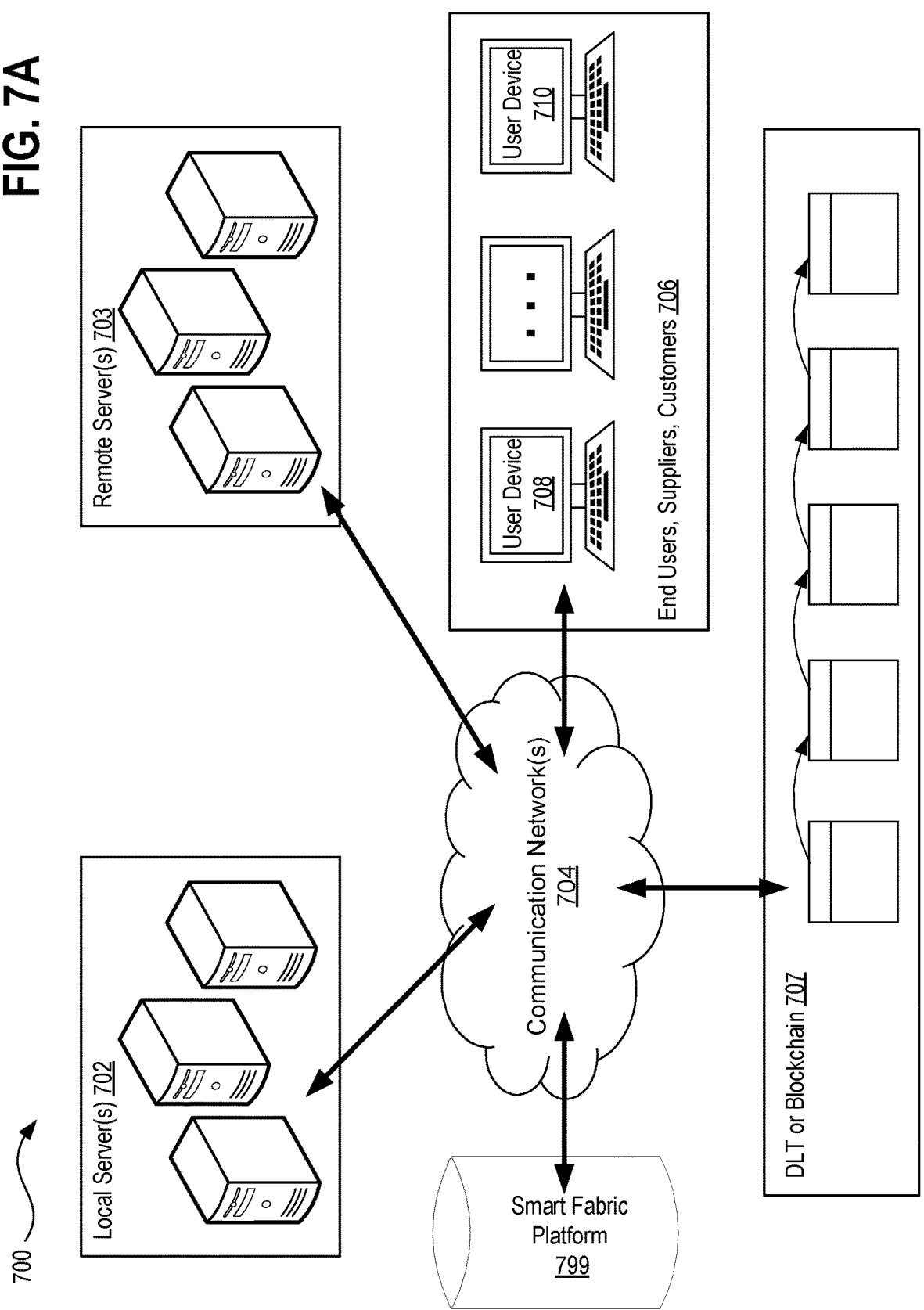
FIG. 7A depicts an exemplary computing architecture upon which the Soil Health Data Fabric platform may operate, in accordance with described embodiments.

FIG. 7A depicts an exemplary computing architecture upon which the Soil Health Data Fabric Platform 101 may operate, in accordance with described embodiments.

In particular, there is depicted here, both local servers 702 and remote servers 703 from which input data may automatically be retrieved and entered on behalf of the Soil Health Data Fabric Platform 101 which may track localized data or remote data respectively on behalf of the Soil Health Data Fabric Platform 101. Additionally, the Soil Health Data Fabric platform 101 provides functionality such as the Artificial Intelligence and Machine Learning functionality by which to implement the soil quality estimate modeling and scaling procedures described herein.

Still further depicted are the devices for end users, suppliers, and customers at element 706 which communicate with the Soil Health Data Fabric Platform 101 and with the local and remote servers (702-703) via the communications network 704. For example, user device 708 may be located at a city department or within an agriculture or farming stakeholder or entity location, such as water management, animal stations, regulators, etc., whereas user device 710 may be located at a food-producing farm, a livestock farm, etc.

According to certain embodiments, data is stored and persisted utilizing DLT or blockchain 707 technologies as is depicted here, and each of the various components such as local servers 702, remote servers 703, the Soil Health Data Fabric Platform 101, and the end users, suppliers, and customers 706 may communicate with the DLT or blockchain 707 technologies to store or retrieve data.

Figure 7B:
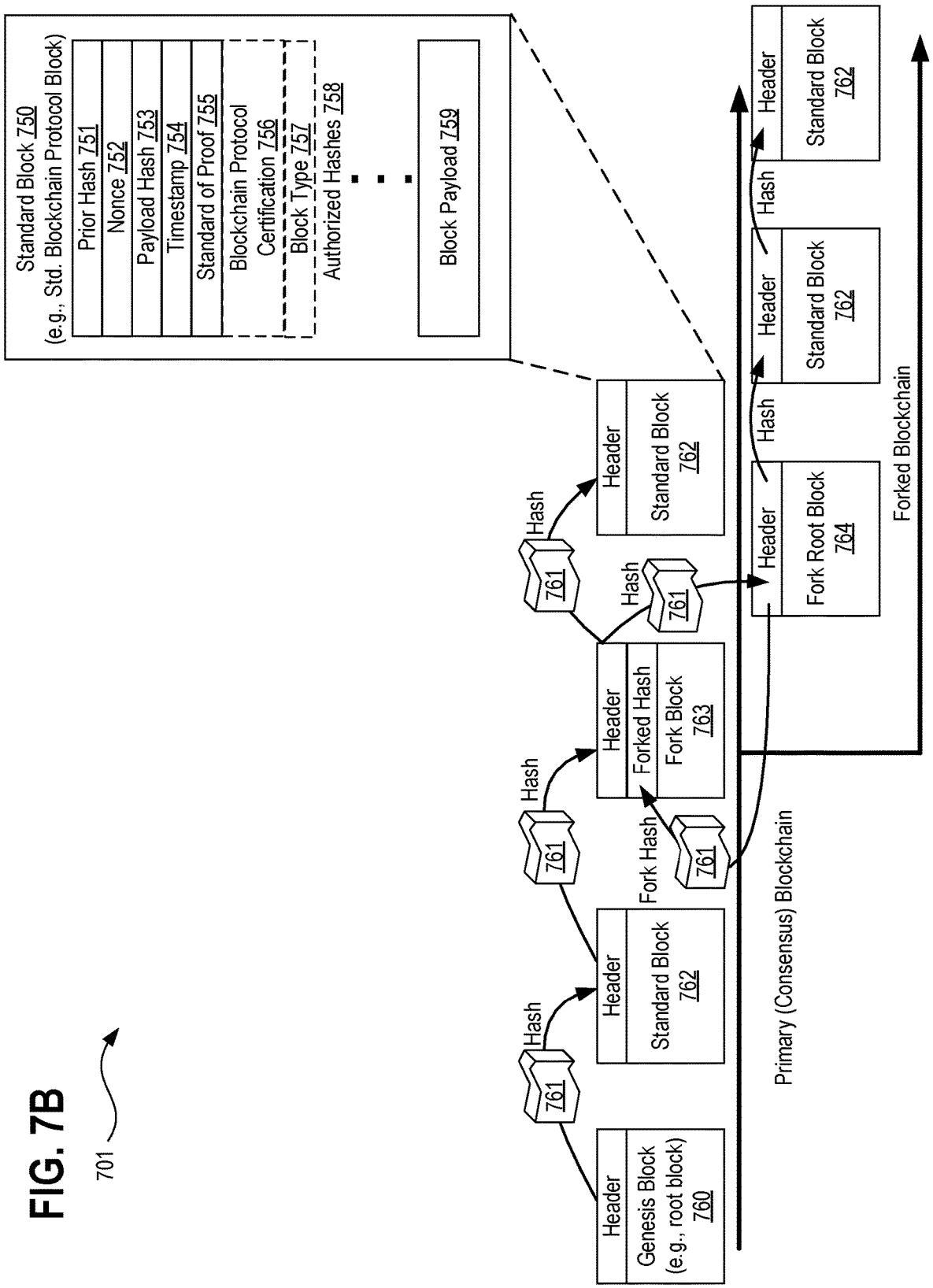
FIG. 7B depicts an exemplary DLT or blockchain architecture, with additional detail of a blockchain standard or protocol block, in accordance with described embodiments.

FIG. 7B depicts an exemplary DLT or blockchain architecture 701, with additional detail of a blockchain standard or protocol block 750, in accordance with described embodiments.

In particular, a blockchain standard or protocol block 750 is depicted here to be validated by, for example, a block validator of a participating node, with the blockchain protocol block including additional detail of its various sub-components, and certain optional elements which may be utilized in conjunction with the blockchain standard or protocol block 750 depending on the particular blockchain protocol being utilized via the Soil Health Data Fabric Platform 101.

A blockchain is a continuously growing list of records, grouped in blocks, which are linked together and secured using cryptography. Each block typically contains a hash pointer as a link to a previous block, a timestamp, and transaction data. By design, blockchains are inherently resistant to modification of the data. A blockchain system essentially is an open, distributed ledger that records transactions between two parties in an efficient and verifiable manner, which is also immutable and permanent. A distributed ledger (also called a shared or common ledger, or referred to as distributed ledger technology (DLT)) is a consensus of replicated, shared, and synchronized digital data geographically spread across multiple nodes. The nodes may be located in different sites, countries, institutions, user communities, companies, departments, or application servers. There is no central administrator or centralized data storage.

Blockchain systems use a peer-to-peer (P2P) network of nodes, and consensus algorithms ensure replication of digital data across nodes. A blockchain system can be either public or private. Not all distributed ledgers necessarily employ a chain of blocks to successfully provide secure and valid achievement of distributed consensus: a blockchain is only one type of data structure considered to be a distributed ledger.

P2P computing or networking is a distributed application architecture that partitions tasks or workloads between peers. Peers are equally privileged, equally capable participants in an application that forms a peer-to-peer network of nodes. Peers make a portion of their resources, such as processing power, disk storage, or network bandwidth, directly available to other network participants, without the need for central coordination by servers or hosts. Peers are both suppliers and consumers of resources, in contrast to the traditional client-server model in which the consumption and supply of resources is divided. A peer-to-peer network is thus designed around the notion of equal peer nodes simultaneously functioning as both clients and servers to the other nodes on the network.

For use as a distributed ledger, a blockchain is typically managed by a peer-to-peer network collectively adhering to a protocol for validating new blocks. Once recorded, the data in any given block cannot be altered retroactively without the alteration of all subsequent blocks, which requires collusion of the network majority. In this manner, blockchains are secure by design and are an example of a distributed computing system with high Byzantine fault tolerance. Decentralized consensus has therefore been achieved with a blockchain. This makes blockchains potentially suitable for the recording of events, medical records, insurance records, and other records management activities, such as identity management, transaction processing, documenting provenance, or voting.

A blockchain database is managed autonomously using a peer-to-peer network and a distributed timestamping server. Records, in the form of blocks, are authenticated in the blockchain by collaboration among the nodes, motivated by collective self-interests. As a result, participants' uncertainty regarding data security is minimized. The use of a blockchain removes the characteristic of reproducibility of a digital asset. It confirms that each unit of value, e.g., an asset, was transferred only once, solving the problem of double spending.

Blocks in a blockchain each hold batches ("blocks") of valid transactions that are hashed and encoded into a Merkle tree. Each block includes the hash of the prior block in the blockchain, linking the two. The linked blocks form a chain. This iterative process confirms the integrity of the previous block, all the way back to the first block in the chain, sometimes called a genesis block or a root block.

By storing data across its network, the blockchain eliminates the risks that come with data being held centrally and controlled by a single authority. The decentralized blockchain may use ad-hoc message passing and distributed networking. The blockchain network lacks centralized points of vulnerability that computer hackers can exploit. Likewise, it has no central point of failure. Blockchain security methods include the use of public-key cryptography. A public key is an address on the blockchain. Value tokens sent across the network are recorded as belonging to that address. A private key is like a password that gives its owner access to their digital assets or the means to otherwise interact with the various capabilities that blockchains support. Data stored on the blockchain is generally considered incorruptible. This is where blockchain has its advantage. While centralized data is more controllable, information and data manipulation are common. By decentralizing it, blockchain makes data transparent to everyone involved.

Every participating node for a particular blockchain protocol within a decentralized system has a copy of the blockchain for that specific blockchain protocol. Data quality is maintained by massive database replication and computational trust. No centralized official copy of the database exists and, by default, no user and none of the participating nodes are trusted more than any other, although this default may be altered via certain specialized blockchain protocols as will be described in greater detail below. Blockchain transactions are broadcast to the network using software, via which any participating node, including the Smart Fabric Platform 499 when operating as a node, receives such transaction broadcasts. Broadcast messages are delivered on a best effort basis. Nodes validate transactions, add them to the block they are building, and then broadcast the completed block to other nodes. Blockchains use various time-stamping schemes, such as proof-of-work, to serialize changes. Alternate consensus may be utilized in conjunction with the various blockchain protocols including, for example, proof-of-stake, proof-of-authority, and proof-of-burn, to name a few.

Open blockchains are more user-friendly than conventional traditional ownership records, which, while open to the public, still require physical access to view. Because most of the early blockchains were permissionless, there is some debate about the specific accepted definition of a so-called "blockchain," such as, whether a private system with verifiers tasked and authorized (permissioned) by a central authority should be considered a blockchain. Proponents of permissioned or private chains argue that the term blockchain may be applied to any data structure that groups data into time-stamped blocks. These blockchains serve as a distributed version of multiversion concurrency control (MVCC) in databases. Just as MVCC prevents two transactions from concurrently modifying a single object in a database, blockchains prevent two transactions from spending the same single output in a blockchain.

An advantage to an open, permissionless, or public, blockchain network is that guarding against bad actors is not required and no access control is needed. This means that applications can be added to the network without the approval or trust of others, using the blockchain as a transport layer. Conversely, permissioned (e.g., private) blockchains use an access control layer to govern who has access to the network. In contrast to public blockchain networks, validators on private blockchain networks are vetted, for example, by the network owner, or one or more members of a consortium. They rely on known nodes to validate transactions. Permissioned blockchains also go by the name of "consortium" or "hybrid" blockchains. Today, many corporations are using blockchain networks with private blockchains, or blockchain-based distributed ledgers, independent of a public blockchain system.

In accordance with a particular embodiment, the blockchain standard or protocol block 750 depicted here defines a particular structure for how the fundamental blocks of any given blockchain protocol are organized.

The prior hash 751 is the result of a non-reversible mathematical computation using data from the prior block 763 as the input. The prior block 763 in turn utilized data from the n previous block(s) 762 to form the non-reversible mathematical computation forming the prior hash for those respective blocks. For instance, according to one embodiment, the non-reversible mathematical computation utilized is a SHA256 hash function, although other hash functions may be utilized. According to such an embodiment, the hash function results in any change to data in the prior block 763 or any of the n previous blocks 762 in the chain, causing an unpredictable change in the hash of those prior blocks, and consequently, invalidating the present or current blockchain protocol block 750. Prior hash 751 creates the link between blocks, chaining them together to form the current blockchain standard or protocol block 750.

When a block validator (e.g., executed by a participating node, etc.) calculates the prior hash 751 for the prior block 763, the hash must meet certain criteria defined by data stored as the standard of proof 755. For instance, in one embodiment, this standard of proof 755 is a number that the calculated hash must be less than. Because the output of the hashing function is unpredictable, it cannot be known before the hash is calculated what input will result in an output that is less than the standard of proof 755. The nonce 752 is used to vary the data content of the block, allowing for a large number of different outputs to be produced by the hash function in pursuit of an output that meets the standard of proof 755, thus making it exceedingly computationally expensive (and therefore statistically improbable) of producing a valid block with a nonce 752 that results in a hash value meeting the criteria of the standard of proof 755.

Payload hash 751 provides a hash of the data stored within the block payload 759 portion of the blockchain protocol block 750 and need not meet any specific standard of proof 755. However, the payload hash is included as part of the input when the hash is calculated for the purpose of storing as the prior hash 751 for the next or subsequent block. Timestamp 754 indicates what time the blockchain protocol block 750 was created within a certain range of error. According to certain blockchain protocol implementations provided via a blockchain services interface, the distributed network of users (e.g., blockchain protocol nodes) checks the timestamp 754 against their own known time and will reject any block having a timestamp 754 which exceeds an error threshold, however, such functionality is optional and may be required by certain blockchain protocols and not utilized by others.

The blockchain protocol certification 756 defines the required size and/or data structure of the block payload 759 as well as certifying compliance with a particular blockchain protocol implementation, and thus, certifies the blockchain protocol that the block subscribes to, as well as implements and honors the particular requirements and configuration options for the indicated blockchain protocol. The blockchain protocol certification 756 may also indicate a version of a given blockchain protocol and the blockchain protocol may permit limited backward and forward compatibility for blocks before nodes will begin to reject new blockchain protocol blocks for non-compliance.

Block type 757 is optional depending on the particular blockchain protocol utilized. Where required for a specific blockchain protocol, a block type 757 must be indicated as being one of an enumerated list of permissible block types 757. Certain blockchain protocols use multiple different block types 757, all of which may have varying payloads, but have a structure which is known a priori according to the blockchain protocol utilized, the declared block type 757, and the blockchain protocol certification 756 certifying compliance with such requirements. Non-compliance or an invalid block type or an unexpected structure or payload for a given declared block type 757 will result in the rejection of that block by network nodes.

Where a variable-sized block payload 759 is utilized, the block type 757 may indicate permissibility of such a variable-sized block payload 759 as well as indicate the index of the first byte in the block payload 759 and the total size of the block payload 759. The block type 757 may be utilized to store other information relevant to the reading, accessing, and correct processing and interpretation of the block payload 759.

Block payload 759 data stored within the block may relate to any number of a wide array of transactional data depending on the particular implementation and blockchain protocol utilized, including payload information related to, for example, financial transactions, ownership information, data access records, document versioning, medical records, voting records, compliance and certification, educational transcripts, purchase receipts, digital rights management records, or literally any kind of data that is storable via a payload of a blockchain protocol block 750, which is essentially any data capable of being digitized. Depending on the particular blockchain protocol chosen, the payload size may be a fixed size or a variable size, which in either case, will be utilized as at least part of the input for the hash that produces the payload hash 753.

Various standard of proofs 755 may be utilized pursuant to the particular blockchain protocol chosen, such as proof of work, hash value requirements, proof of stake, a key, or some other indicator such as a consensus, or proof of consensus. Where consensus-based techniques are utilized, a blockchain consensus manager may provide consensus management on behalf of certain participating nodes or on behalf of the Soil Health Data Fabric Platform 101, however, the Soil Health Data Fabric Platform 101 may be operating only as one of many nodes for a given blockchain protocol which is accessed by the Soil Health Data Fabric Platform 101 via, for example, a blockchain services interface. Such a standard of proof 755 may be applied as a rule that requires a hash value to be less than the proof standard, more than the proof standard, or may require a specific bit sequence (such as 10 zeros, or a defined binary sequence) or a required number of leading or trailing zeroes (e.g., such as a hash of an input which results in 20 leading or trailing zeros, which is computationally infeasible to provide without a known valid input).

The hash algorithms used for the prior hash 751, the payload hash 753, or the authorized hashes 758 may all be of the same type or of different types, depending on the particular blockchain protocol implementation. For instance, permissible hash functions include MD5, SHA-1, SHA-224, SHA-256, SHA-384, SHA-515, SHA-515/224, SHA-515/256, SHA-3, or any suitable hash function resistant to pre-image attacks. There is also no requirement that a hash is computed only once. The results of a hash function may be reused as inputs into another or the same hash function again multiple times in order to produce a final result.

Further depicted is a forked blockchain, branching from the primary blockchain (e.g., a consensus blockchain) which begins with a genesis block 760 (sometimes called a root block) followed by a series of standard blocks 762, each having a header which is formed based at least in part from a hash of the header of the block which precedes it. There is additionally depicted the forked blockchain formed with the initial fork root block 764, followed by then a series of standard blocks 762. Because each block in the blockchain contains a hash of the immediately preceding block stored in the previous hash, a link going back through the chain from each block is effectively created via the blockchain and is a key component to making it prohibitively difficult or computationally infeasible to maliciously modify the chain.

As depicted, the primary blockchain includes a single fork which is originating from the fork block 763. As shown here, the genesis block 760 is a special block that begins the primary blockchain and is different from the other blocks because it is the first block in the primary blockchain and therefore, cannot by definition, include a hash of any previous block. The genesis block 760 marks the beginning of the primary blockchain for the particular blockchain protocol being utilized. The blockchain protocol governs the manner by which the primary blockchain grows, what data may be stored within, and forked blockchains are created, as well as the validity of any block and any chain may be verified via a block validator or any other participating network node of the blockchain pursuant to the rules and requirements set forth by the blockchain protocol certification 756 which is embedded within the genesis block 760 and then must be certified to and complied with by every subsequent block in the primary blockchain or any forked blockchain.

The blockchain protocol certification 756 inside each block in the genesis chain defines the default set of rules and configuration parameters that allows for the creation of forks and the modification of rules and configuration parameters in those forks, if any. Some blockchain protocol implementations permit no variation or non-compliance with the default set of rules as established via the blockchain protocol certification 756 and therefore, any fork will be the result of pending consensus for multiple competing potentially valid primary blockchains. Once consensus is reached (typically after one or two cycles and new block formations) then the branch having consensus will be adopted and the fork truncated, thus returning to a single primary consensus blockchain. Conversely, in other implementations, a forked blockchain may permissibly be created and continue to exist indefinitely alongside the primary blockchain, so long as the forked blockchain complies with the blockchain protocol certification 756 and permissible variation of rules and configuration parameters for a forked blockchain within that blockchain protocol.

Fork block 763 anchors the forked blockchain to the primary blockchain such that both the primary blockchain and the forked chain are considered valid and permissible chains where allowed pursuant to the blockchain protocol certification 756. Normally, in a blockchain, all non-consensus forks are eventually ignored or truncated and thus considered invalid except for the one chain representing the longest chain having consensus. Nevertheless, the fork block 763 expands beyond the conventional norms of prior blockchain protocols by operating as and appearing as though it is a standard block 762, while additionally including a reference to a fork hash 761 identifying the first block of the permissible forked blockchain, represented here as the fork root block 764 for the valid forked blockchain. The fork root block 764 of the forked blockchain is then followed by standard blocks, each having a header based on a prior valid block's hash, and will continue indefinitely.

Under normal operating conditions, even conventional blockchains naturally fork from time to time, however, with previously known blockchains, ultimately only a single branch may form the primary consensus chain and all other forks must be ignored or truncated with only the primary consensus blockchain being considered as valid. Consensus on which chain is valid may be achieved by choosing the longest chain, which thus represents the blockchain having the most work put into completing it. Therefore, it is necessary to utilize the fork block 763 as described herein to permit permissibly forked chains to be created and certified as authorized forks via the fork hash 761 so as to prevent participating nodes to ignore or truncate the fork. Because each node may independently validate the forked blockchain, it will not be ignored, just as a validated primary blockchain will not be ignored upon having consensus.

According to yet other embodiments, farmer-supplied data 107 may be provisioned onto blockchain 701 to contribute payload data via a producer app. The producer app may serve as an interface for multiple inputs into a single asset on the blockchain. The producer app is a lightweight interface that allows farmers, ranchers, landowners to contribute information directly to the smart farm fabric. According to certain embodiments, farm equipment may be turned into Internet of things (IoT) objects through embedded sensors on for example a tractor that connects to the producer app and contributes data to the blockchain.

As previously described blockchain allows for data encryption and security. Data can not only be contributed directly via the producer app, but data may be tracked and traced to provide an audit trail of contribution and usage transparency. Public and private keys allow for the secure contribution of data from farmers, farm equipment, etc., and for the cryptographic sealing of data for sharing only with approved users.

Unique Transit and Transfer Functionality on a Blockchain.

Blockchain 701 allows for track and trace of inputs such as inputs 103 and combining them with soil sample baselines 105 as appropriate to create a carbon/greenhouse gas footprint for a given square meter or parcel of land. The transit functionality is the core representation on blockchain 701 for a particular farmer and tracks and aggregates inputs from that particular landowner about a particular parcel of land. The transfer functionality is the piece that tracks inputs from one landowner to another landowner or one farm to another. According to certain embodiments, the transfer functionality may be used in scaling soil health quality to larger areas of land.

Through the use of blockchain and related "Distributed Ledger Technologies" or DLT based technologies, it is further possible to allow the soil health data collected by a variety of first party sources to be captured, stored, and co-located within a common platform, such as a common blockchain accessible to such first party sources. For instance, each of the first party sources may operate as a node of the blockchain with both write access to the blockchain to contribute such data as well as consensus and voting authority, thus enabling those first party sources to perform validation of data stored to the commonly accessible blockchain.

According to described embodiments, such data sources may be from soil samples, flux towers, satellite imagery, farming equipment and other machines, any of which may be directly interfaced to an appropriate API or other receive interface so as to facilitate IoT communications for the sake of fully automated data capture. Similarly, such data sources may be the result of manual inputs from landowners and farm operators via, for example, a land owner application. Once received, the first party data contributed to and captured by the blockchain is then able to be triangulated and validated with other data inputs through the use of these blockchain technologies.

FIG. 8 illustrates a diagrammatic representation of a machine 801 in the exemplary form of a computer system, in accordance with one embodiment, within which a set of instructions, for causing the machine/computer system 801 to perform any one or more of the methodologies discussed herein, may be executed. In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 801 includes a processor 802, a main memory 804 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 818 (e.g., a persistent storage device including hard disk drives and a persistent database and/or a multi-tenant database implementation), which communicate with each other via a bus 830. Main memory 804 includes various specialized components and computing architecture circuitry including the Smart City/Smart Farm Fabric logic 824 (e.g., via which data integration for the Smart City Fabric data and Smart Farm Fabric data are facilitated), the Soil Health Data Fabric logic 523 (e.g., via which Soil Health Data Fabric data integration is facilitated), and the analytical model for continuous learning 825 via which the system is specially configured to continuously consume, aggregate, analyze and ultimately learn and optimize improvements and operational parameters for the smart fabric implementations in support of the methodologies and techniques described herein. Main memory 804 and its sub-elements are further operable in conjunction with processing logic 826 and processor 802 to perform the methodologies discussed herein.

Processor 802 represents one or more specialized and specifically configured processing devices such as a microprocessor, central processing unit, or the like. More particularly, the processor 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 802 may also be one or more special-purpose processing devices such as an application-specific integrated circuit (ASIC), a field-programmable gate array (FPGA), a digital signal processor (DSP), network processor, or the like. Processor 802 is configured to execute the processing logic 826 for performing the operations and functionality which is discussed herein.

The computer system 801 may further include a network interface card 808. The computer system 801 also may include a user interface 810 (such as a video display unit, a liquid crystal display, etc.), an alphanumeric input device 812 (e.g., a keyboard), a cursor control device 813 (e.g., a mouse), and a signal generation device 816 (e.g., an integrated speaker). The computer system 801 may further include peripheral device 836 (e.g., wireless or wired communication devices, memory devices, storage devices, audio processing devices, video processing devices, etc.).

The secondary memory 818 may include a non-transitory machine-readable storage medium or a non-transitory computer-readable storage medium or a non-transitory machine-accessible storage medium 831 on which is stored one or more sets of instructions (e.g., software 822) embodying any one or more of the methodologies or functions described herein. The software 822 may also reside, completely or at least partially, within the main memory 804 and/or within the processor 802 during execution thereof by the computer system 801, the main memory 804, and the processor 802 also constituting machine-readable storage media. The software 822 may further be transmitted or received over a network 520 via the network interface card 808.

According to a particular embodiment, there is a system for implementing automated data modeling and scaling of a soil health data fabric, wherein the system comprises: a memory to store instructions; a processor to execute instructions stored in the memory; and stored logic within the memory that, when executed by the processor, causes the processor to perform operations including: compiling data measurements from disparate soil health data sources at a plurality of training data sites into a blockchain repository; integrating the data measurements with one or more of: (i) a plurality of baseline soil samples, and (ii) satellite imagery related to the plurality of training data sites to correlate soil health; training an AI algorithm using the integrated data measurements to determine most accurate local soil quality estimates; executing the AI algorithm, via a machine learning toolbox interfaced with an ecosystem soil dynamics engine, to output a plurality of soil quality estimate data models based on the data measurements, in which the plurality of local soil quality estimate data models are based on pre-determined soil quality indicators; training the local soil quality estimate data models by comparing the local soil quality estimate data models to the plurality of soil samples; refining the local soil quality estimate data models via feedback processing to generate a regional soil quality estimate data model, in which the feedback processing applies transfer learning and feedback using additional data and comparison to the plurality of soil samples; scaling the local and regional soil quality estimate data models; and outputting soil quality estimates for a target region based on extended satellite imagery.

Figure 9A:
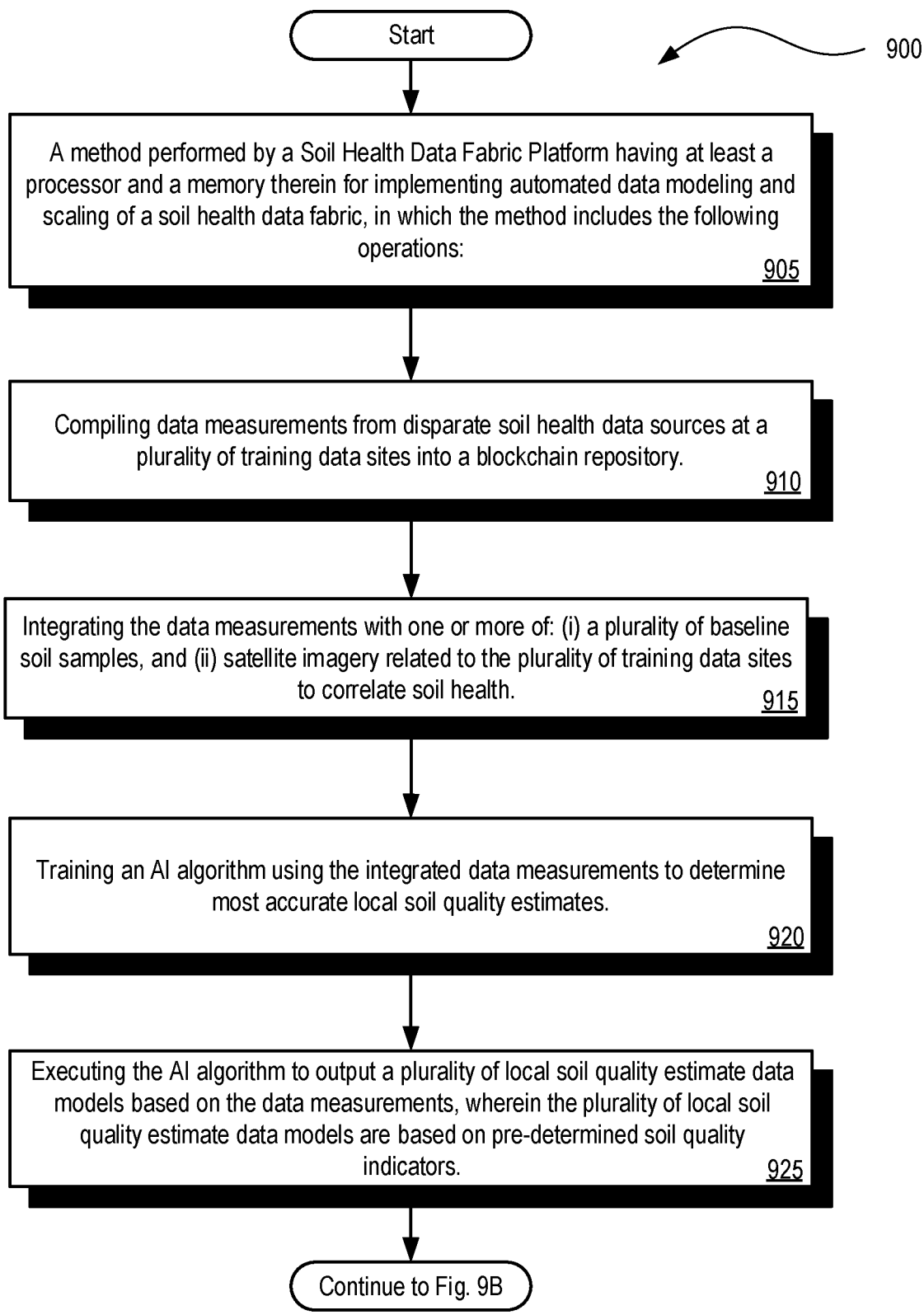
FIGS. 9A-9B depict a flow diagram illustrating a method for implementing automated data modeling and scaling of a Soil Health Data Fabric, in accordance with disclosed embodiments.
Figure 9B:
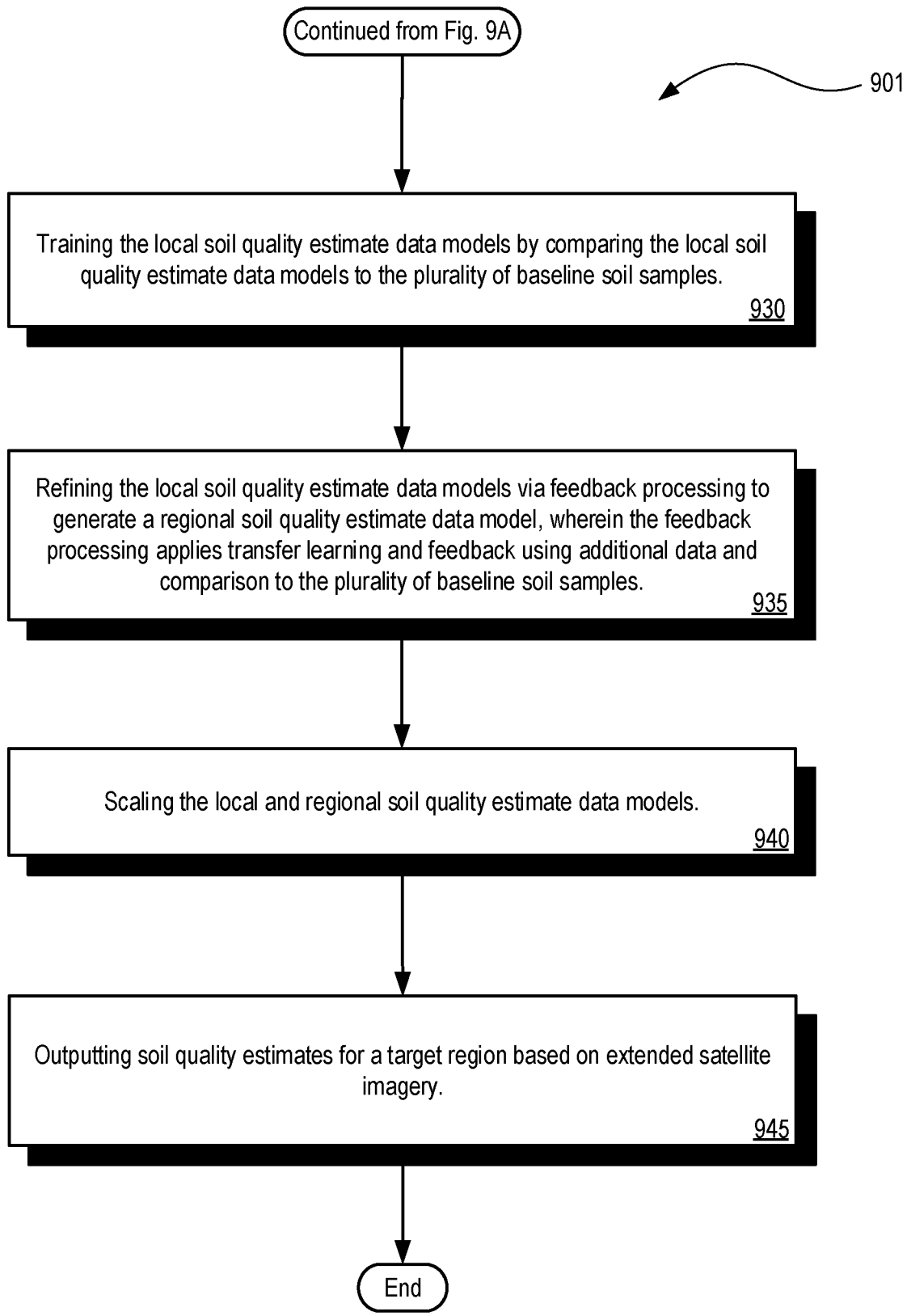

FIGS. 9A-9B depicts a flow diagram illustrating a method 900-901 for implementing automated data modeling and scaling of a soil health data fabric, in accordance with disclosed embodiments. Method 900-901 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, machine 801 (see FIG. 8) and the other supporting systems and components as described herein may implement the described methodologies. Some of the blocks and/or operations listed below are optional, in accordance with certain embodiments. The numbering of the blocks presented is for the sake of clarity and is not intended to prescribe an order of operations in which the various blocks must occur.

With reference to the method 900-901 depicted at FIG. 9A beginning at block 905, there is a method performed by a Soil Health Data Fabric Platform having at least a processor and a memory therein for implementing automated data modeling and scaling of a soil health data fabric, in which the method includes the following operations:

At block 910, processing logic compiles data measurements from disparate soil health data sources at a plurality of training data sites into a blockchain repository.

At block 915, processing logic integrates the data measurements with one or more of: (i) a plurality of baseline soil samples, and (ii) satellite imagery related to the plurality of training data sites to correlate soil health.

At block 920, processing logic trains an AI algorithm using the integrated data measurements to determine most accurate local soil quality estimates.

At block 925, processing logic outputs a plurality of local soil quality estimate data models based on the data measurements, in which the plurality of local soil quality estimates data models are based on pre-determined soil quality indicators.

Method 900-901 continues at FIG. 9B.

With reference to the method 900-901 depicted at FIG. 9B beginning at block 930, processing logic trains the local soil quality estimate data models by comparing the local soil quality estimate data models to the plurality of baseline soil samples.

At block 935, processing logic refines the local soil quality estimate data models via feedback processing to generate a regional soil quality estimate data model, in which the feedback processing applies transfer learning and feedback using additional data and comparison to the plurality of baseline soil samples.

At block 940, processing logic scales the local and regional soil quality estimate data models.

Finally, at block 945, processing logic outputs soil quality estimates for a target region based on extended satellite imagery.

According to another embodiment of method 900-901, the data measurements from disparate soil health data sources include one or more of: (i) satellite data, (ii) soil sample baselines, and (iii) flux tower data, wherein the flux tower data includes data transmitted from one or more of: (i) farmers, (ii) ranchers, (iii) landowners, and (iv) agricultural equipment.

According to another embodiment of method 900-901, the pre-determined soil quality indicators include one or more of: (i) organic matter cycling and carbon sequestration based on soil organic carbon content, (ii) soil structural stability based on water-stable aggregates, (iii) general microbial activity based on short-term carbon mineralization, (iv) carbon food source based on measurements of active carbon, (v) bioavailable nitrogen based on extracted organic matter protein, and (vi) microbial biomass and community composition based on fatty acids.

According to another embodiment of method 900-901, the target region differs in one or more of: (i) soil composition, (ii) climate, (iii) region, and (iv) topography in comparison to the training data sites.

According to another embodiment of method 900-901, the additional data includes one or more of: (i) soil, (ii) slope, (iii) geographic, (iv) geophysical, (v) genomic, and (vi) aggregated data.

According to another embodiment of method 900-901, the most accurate local soil quality estimates are determined based on: (i) soil physics, (ii) soil chemistry, (iii) soil biology, and (iv) fractal geometry.

According to another embodiment of method 900-901, compiling data measurements from disparate soil health data sources at a plurality of training data sites into a blockchain repository is mediated by a producer app allowing direct input of data measurements from one or more of: (i) users including farmers, ranchers, and landowners, and (ii) agricultural equipment having Internet of Things (IoT) capabilities.

According to another embodiment of method 900-901, compiling data measurements from disparate soil health data sources at a plurality of training data sites into a blockchain repository provides track and trace functionality for encrypting and auditing input of and access to the data measurements.

According to another embodiment of method 900-901, compiling data measurements from disparate soil health data sources at a plurality of training data sites into a blockchain repository generates a single asset on the blockchain repository.

According to another embodiment of method 900-901, the local and regional soil quality estimation models are further refined for evaluation of model accuracy by application to a test data site via model transfer and synthetic data using additional data.

According to another embodiment of method 900-901, integrating the data measurements with one or more of: (i) a plurality of baseline soil samples, and (ii) satellite imagery related to the plurality of training data sites to correlate soil health includes correlating soil health with foliage data from the satellite imagery.

According to another embodiment of method 900-901, the AI algorithm is executed via a machine learning toolbox interfaced with an ecosystem soil dynamics engine.

According to a particular embodiment, there is a non-transitory computer readable storage medium having instructions stored thereupon that, when executed by a Soil Health Data Fabric Platform having at least a processor and a memory therein, the instructions cause the Soil Health Data Fabric Platform to perform operations including: compiling data measurements from disparate soil health data sources at a plurality of training data sites into a blockchain repository; integrating the data measurements with one or more of: (i) a plurality of baseline soil samples, and (ii) satellite imagery related to the plurality of training data sites to correlate soil health; training an AI algorithm using the integrated data measurements to determine most accurate local soil quality estimates; executing the AI algorithm to output a plurality of soil quality estimate data models based on the data measurements, in which the plurality of local soil quality estimate data models are based on pre-determined soil quality indicators; training the local soil quality estimate data models by comparing the local soil quality estimate data models to the plurality of soil samples; refining the local soil quality estimate data models via feedback processing to generate a regional soil quality estimate data model, in which the feedback processing applies transfer learning and feedback using additional data and comparison to the plurality of soil samples; scaling the local and regional soil quality estimate data models; and outputting soil quality estimates for a target region based on extended satellite imagery.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as would be apparent to those skilled in the art. Therefore, the scope of the appended claims should be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system including a convolutional neural network to predict soil quality estimates for a target region using data measurements for a soil health data fabric, the system comprising:
   a memory configured to store the data measurements for the soil health data fabric; and
   processing circuitry in communication with the memory, wherein the processing circuitry is configured to:
      compile the data measurements from disparate soil health data sources at a plurality of training data sites into a blockchain repository;
      combine, using a track and trace function of the blockchain repository, the data measurements with inputs including at least a plurality of baseline soil samples, and satellite imagery related to the plurality of training data sites to correlate soil health;
      train, by the system, the convolutional neural network, based on the data measurements combined with the inputs using a selected machine learning algorithm to generate a trained artificial intelligence model, wherein the selected machine learning algorithm includes transfer learning and feedback processing;
      execute the selected machine learning algorithm to update the trained artificial intelligence model using the transfer learning to generate a plurality of local soil quality estimates based on determined local soil quality estimates transferred from the data measurements combined with the inputs, wherein the plurality of local soil quality estimates are based on pre-determined soil quality indicators;
      update the local soil quality estimates of the trained artificial intelligence model using the feedback processing to generate a regional soil quality estimate, wherein to update the local soil quality estimates of the trained artificial intelligence model includes application of the transfer learning and the feedback processing to update the trained artificial intelligence model using additional data in comparison to the plurality of baseline soil samples;
      scale, by the trained artificial intelligence model, the local soil quality estimates and the regional soil quality estimate; and
      output, by the trained artificial intelligence model, the soil quality estimates for the target region based on extended satellite imagery.

2. The system of claim 1, wherein to execute the machine learning algorithm includes the processing circuitry further configured to execute the machine learning algorithm from a user interface to output the plurality of local soil quality estimates based on the data measurements using measured soil physics, soil chemistry, soil biology, and and/or fractal geometry measurements for the soil.

3. The system of claim 1, wherein the data measurements from disparate soil health data sources include one or more of: (i) satellite data, (ii) soil sample baselines, and (iii) flux tower data, wherein the flux tower data includes data transmitted from one or more of: (i) farmers, (ii) ranchers, (iii) landowners, and (iv) agricultural equipment.

4. The system of claim 1, wherein the pre-determined soil quality indicators include one or more of: (i) organic matter cycling and carbon sequestration based on soil organic carbon content, (ii) soil structural stability based on water-stable aggregates, (iii) general microbial activity based on short-term carbon mineralization, (iv) carbon food source based on measurements of active carbon, (v) bioavailable nitrogen based on extracted organic matter protein, and (vi) microbial biomass and community composition based on fatty acids.

5. The system of claim 1, wherein the target region differs in one or more of: (i) soil composition, (ii) climate, (iii) region, and (iv) topography in comparison to the plurality of training data sites.

6. The system of claim 1, wherein the additional data includes one or more of: (i) soil, (ii) slope, (iii) geographic, (iv) geophysical, (v) genomic, and (vi) aggregated data.

7. The system of claim 1, wherein the determined local soil quality estimates are determined based on: (i) soil physics, (ii) soil chemistry, (iii) soil biology, and (iv) fractal geometry.

8. The system of claim 1, wherein to compile the data measurements from the disparate soil health data sources at the plurality of training data sites into the blockchain repository includes the processing circuitry further configured to obtain the data measurements from one or more of: users including farmers, ranchers, and landowners, and agricultural equipment having Internet of Things (IoT) capabilities.

9. The system of claim 1, wherein to compile the data measurements from the disparate soil health data sources at the plurality of training data sites into a blockchain repository includes the processing circuitry further configured to provide track and trace functionality for encrypting and auditing input of and access to the data measurements.

10. The system of claim 1, wherein to compile the data measurements from the disparate soil health data sources at the plurality of training data sites into the blockchain repository includes the processing circuitry further configured to generate a single asset on the blockchain repository.

11. The system of claim 1, wherein the processing circuitry is further configured to update the local soil quality estimates and the regional soil quality estimate for evaluation of accuracy by application of the local soil quality estimates and the regional soil quality estimate to a test data site using model transfer and synthetic data generation using the additional data.

12. The system of claim 1, wherein the processing circuitry is further configured to correlate soil health with foliage data from the satellite imagery.

13. The system of claim 1, wherein the machine learning algorithm is executable via a user interface.

14. A method of predicting soil quality estimates for a target region using data measurements for a soil health data fabric using a convolutional neural network, the method comprising:
   compiling data measurements from disparate soil health data sources at a plurality of training data sites into a blockchain repository;
   combining, using a track and trace function of the blockchain repository, the data measurements with inputs including at least a plurality of baseline soil samples, and satellite imagery related to the plurality of training data sites to correlate soil health;
   training the convolutional neural network based on the data measurements combined with the inputs using a selected machine learning algorithm to generate a trained artificial intelligence model, wherein the selected machine learning algorithm includes transfer learning and feedback processing;

executing the selected machine learning algorithm to update the trained artificial intelligence model using the transfer learning to generate a plurality of local soil quality estimates based on determined local soil quality estimates transferred from the data measurements combined with the inputs, wherein the plurality of local soil quality estimates are based on pre-determined soil quality indicators;

updating the local soil quality estimates of the trained artificial intelligence model using the feedback processing to generate a regional soil quality estimate, wherein to update the local soil quality estimates of the trained artificial intelligence model includes application of the transfer learning and the feedback processing to update the trained artificial intelligence model using additional data in comparison to the plurality of baseline soil samples;

scaling, using the trained artificial intelligence model, the local soil quality estimates and the regional soil quality estimate; and outputting, using the trained artificial intelligence model, the soil quality estimates for the target region based on extended satellite imagery.

15. The method of claim 14, wherein the pre-determined soil quality indicators include one or more of: (i) organic matter cycling and carbon sequestration based on soil organic carbon content, (ii) soil structural stability based on water-stable aggregates, (iii) general microbial activity based on short-term carbon mineralization, (iv) carbon food source based on measurements of active carbon, (v) bioavailable nitrogen based on extracted organic matter protein, and (vi) microbial biomass and community composition based on fatty acids.

16. The method of claim 14:
wherein the target region differs in one or more of: (i) soil composition, (ii) climate, (iii) region, and (iv) topography in comparison to the plurality of training data sites;
wherein the additional data includes one or more of: (i) soil, (ii) slope, (iii) geographic, (iv) geophysical, (v) genomic, and (vi) aggregated data; and
wherein the determined local soil quality estimates are determined based on: (i) soil physics, (ii) soil chemistry, (iii) soil biology, and (iv) fractal geometry.

17. The method of claim 14: wherein compiling data measurements from the disparate soil health data sources at the plurality of training data sites into the blockchain repository includes obtaining the data measurements from one or more of: users including farmers, ranchers, and landowners, and agricultural equipment having Internet of Things (IoT) capabilities;
wherein compiling the data measurements from disparate soil health data sources at the plurality of training data sites into a blockchain repository enables the track and trace function for encrypting and auditing input of and access to the data measurements; and
wherein compiling data measurements from the disparate soil health data sources at the plurality of training data sites into the blockchain repository generates a single asset on the blockchain repository.

18. Non-transitory computer-readable storage media having instructions stored thereupon that, when executed, cause processing circuitry to:

compile data measurements from disparate soil health data sources at a plurality of training data sites into a blockchain repository;

combine, using a track and trace function of the blockchain repository, the data measurements with inputs including at least a plurality of baseline soil samples, and satellite imagery related to the plurality of training data sites to correlate soil health;

train, by the processing circuitry, a convolutional neural network, based on the data measurements combined with the inputs using a selected machine learning algorithm to generate a trained artificial intelligence model, wherein the selected machine learning algorithm includes transfer learning and feedback processing;

execute the selected machine learning algorithm to update the trained artificial intelligence model using the transfer learning to generate a plurality of local soil quality estimates based on determined local soil quality estimates transferred from the data measurements combined with the inputs, wherein the plurality of local soil quality estimates are based on pre-determined soil quality indicators;

update the local soil quality estimates of the trained artificial intelligence model using the feedback processing to generate a regional soil quality estimate, wherein to update the local soil quality estimates of the trained artificial intelligence model includes application of the transfer learning and the feedback processing to update the trained artificial intelligence model using additional data in comparison to the plurality of baseline soil samples;

scale, by the trained artificial intelligence model, the local soil quality estimates and the regional soil quality estimate; and output, by the trained artificial intelligence model, soil quality estimates for a target region based on extended satellite imagery.

19. The non-transitory computer-readable storage media of claim 18: wherein the target region differs in one or more of: (i) soil composition, (ii) climate, (iii) region, and (iv) topography in comparison to the plurality of training data sites;
wherein the additional data includes one or more of: (i) soil, (ii) slope, (iii) geographic, (iv) geophysical, (v) genomic, and (vi) aggregated data; and
wherein the determined local soil quality estimates are determined based on: (i) soil physics, (ii) soil chemistry, (iii) soil biology, and (iv) fractal geometry.

20. The non-transitory computer-readable storage media of claim 18, wherein the instructions, when executed, further cause the processing circuitry to:
obtain the inputs from one or more of: (i) users including farmers, ranchers, and landowners, and (ii) agricultural equipment having Internet of Things (IoT) capabilities;
enable track and trace functionality of the blockchain repository for encrypting and auditing input of and access to the data measurements; and
wherein to compile the data measurements from the disparate soil health data sources at the plurality of training data sites into the blockchain repository includes the instructions, when executed, to further cause the processing circuitry to generate a single asset on the blockchain repository.

* * * * *